(12) United States Patent
Bates et al.

(10) Patent No.: US 8,059,923 B2
(45) Date of Patent: Nov. 15, 2011

(54) SYSTEMS AND METHODS FOR MINIMALLY-INVASIVE OPTICAL-ACOUSTIC IMAGING

(75) Inventors: Kenneth N. Bates, Beaverton, OR (US); Gil M. Vardi, Town & Country, MO (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 17 days.

(21) Appl. No.: 12/701,228

(22) Filed: Feb. 5, 2010

(65) Prior Publication Data

US 2010/0135111 A1    Jun. 3, 2010

Related U.S. Application Data

(63) Continuation of application No. 12/263,978, filed on Nov. 3, 2008, now Pat. No. 7,660,492, which is a continuation of application No. 11/674,568, filed on Feb. 13, 2007, now Pat. No. 7,447,388, which is a continuation of application No. 10/266,082, filed on Oct. 7, 2002, now Pat. No. 7,245,789.

(51) Int. Cl.
*G02F 1/355* (2006.01)
*G01V 1/145* (2006.01)

(52) U.S. Cl. ............................ 385/7; 367/189

(58) Field of Classification Search ........ 385/7; 367/189
See application file for complete search history.

(56) References Cited

U.S. PATENT DOCUMENTS

| | | | |
|---|---|---|---|
| 4,068,191 A | 1/1978 | Zemon et al. | |
| 4,076,379 A | 2/1978 | Chouinard | |
| 4,115,753 A | 9/1978 | Shajenko | |
| 4,473,065 A | 9/1984 | Bates | |
| 4,522,193 A | 6/1985 | Bates | |
| 4,587,972 A | 5/1986 | Morantte, Jr. | |
| 4,887,605 A | 12/1989 | Angelsen et al. | |

(Continued)

FOREIGN PATENT DOCUMENTS

CA    2472877    7/2003

(Continued)

OTHER PUBLICATIONS

"U.S. Appl. No. 09/623,248, Notice of Allowance mailed Jan. 13, 2003", 7 pgs.

(Continued)

*Primary Examiner* — Jerry Rahll
(74) *Attorney, Agent, or Firm* — Schwgman, Lundberg & Woessner, P.A.

(57) ABSTRACT

An imaging guidewire can include one or more optical fibers communicating light along the guidewire. At or near its distal end, one or more blazed or other fiber Bragg gratings (FBGs) directs light to a photoacoustic transducer material that provides ultrasonic imaging energy. Returned ultrasound is sensed by an FBG sensor. A responsive signal is optically communicated to the proximal end of the guidewire, and processed to develop a 2D or 3D image. In one example, the guidewire outer diameter is small enough such that an intravascular catheter can be passed over the guidewire. Techniques for improving ultrasound reception include using a high compliance material, resonating the ultrasound sensing transducer, using an attenuation-reducing coating and/or thickness, and/or using optical wavelength discrimination. Techniques for improving the ultrasound generating transducer include using a blazed FBG, designing the photoacoustic material thickness to enhance optical absorption. Techniques for distinguishing plaque or vulnerable plaque may be used to enhance the displayed image.

29 Claims, 11 Drawing Sheets

U.S. PATENT DOCUMENTS

| | | |
|---|---|---|
| 4,900,921 A | 2/1990 | Spillman, Jr. |
| 4,917,097 A | 4/1990 | Proudian et al. |
| 4,946,238 A | 8/1990 | Sashin et al. |
| 5,007,705 A | 4/1991 | Morey et al. |
| 5,070,882 A | 12/1991 | Bui et al. |
| 5,095,911 A | 3/1992 | Pomeranz |
| 5,099,090 A | 3/1992 | Allan et al. |
| 5,109,463 A | 4/1992 | Lee |
| 5,135,295 A | 8/1992 | Jen et al. |
| 5,135,486 A | 8/1992 | Eberle et al. |
| 5,156,772 A | 10/1992 | Allan |
| 5,167,233 A | 12/1992 | Eberle et al. |
| 5,183,048 A | 2/1993 | Eberle |
| 5,186,177 A | 2/1993 | O'Donnell et al. |
| 5,226,847 A | 7/1993 | Thomas, III et al. |
| 5,240,004 A | 8/1993 | Walinsky et al. |
| 5,254,112 A | 10/1993 | Sinofsky et al. |
| 5,290,275 A | 3/1994 | Kittrell et al. |
| 5,305,758 A | 4/1994 | Dietz et al. |
| 5,368,037 A | 11/1994 | Eberle et al. |
| 5,383,467 A | 1/1995 | Auer et al. |
| 5,400,788 A | 3/1995 | Dias et al. |
| 5,427,107 A | 6/1995 | Milo et al. |
| 5,439,000 A | 8/1995 | Gunderson et al. |
| 5,453,575 A | 9/1995 | O'Donnell et al. |
| 5,486,170 A | 1/1996 | Winston et al. |
| 5,558,669 A | 9/1996 | Reynard |
| 5,582,171 A | 12/1996 | Chornenky et al. |
| 5,601,087 A | 2/1997 | Gunderson et al. |
| 5,603,327 A | 2/1997 | Eberle et al. |
| 5,615,675 A | 4/1997 | O'Donnell et al. |
| 5,660,180 A | 8/1997 | Malinowski et al. |
| 5,675,674 A | 10/1997 | Weis |
| 5,680,489 A | 10/1997 | Kersey |
| 5,682,897 A | 11/1997 | Pomeranz |
| 5,684,297 A | 11/1997 | Tardy |
| 5,704,361 A | 1/1998 | Seward et al. |
| 5,718,226 A | 2/1998 | Riza |
| 5,732,046 A | 3/1998 | O'Donnell et al. |
| 5,748,564 A | 5/1998 | Pattanayak |
| 5,779,643 A | 7/1998 | Lum et al. |
| 5,779,644 A | 7/1998 | Eberle et al. |
| 5,830,145 A | 11/1998 | Tenhoff |
| 5,852,233 A | 12/1998 | Arnold et al. |
| 5,857,974 A | 1/1999 | Eberle et al. |
| 5,865,178 A | 2/1999 | Yock |
| 5,872,879 A | 2/1999 | Hamm |
| 5,876,344 A | 3/1999 | Baker et al. |
| 5,894,531 A | 4/1999 | Alcoz |
| 5,921,931 A | 7/1999 | O'Donnell et al. |
| 5,938,609 A | 8/1999 | Pomeranz |
| 5,938,615 A | 8/1999 | Eberle et al. |
| 5,944,687 A | 8/1999 | Benett et al. |
| 5,980,117 A | 11/1999 | Feuer et al. |
| 6,039,701 A | 3/2000 | Sliwa et al. |
| 6,049,958 A | 4/2000 | Eberle et al. |
| 6,057,927 A | 5/2000 | Levesque et al. |
| 6,078,831 A | 6/2000 | Belef et al. |
| 6,080,109 A | 6/2000 | Baker et al. |
| 6,100,969 A | 8/2000 | Perez |
| 6,111,645 A | 8/2000 | Tearney et al. |
| 6,123,673 A | 9/2000 | Eberle et al. |
| 6,134,003 A | 10/2000 | Tearney et al. |
| 6,210,339 B1 | 4/2001 | Kiepen et al. |
| 6,222,970 B1 | 4/2001 | Wach et al. |
| 6,228,078 B1 | 5/2001 | Eggers et al. |
| 6,238,347 B1 | 5/2001 | Nix et al. |
| 6,248,076 B1 | 6/2001 | White et al. |
| 6,261,246 B1 | 7/2001 | Pantages et al. |
| 6,282,011 B1 | 8/2001 | Tearney et al. |
| 6,283,920 B1 | 9/2001 | Eberle et al. |
| 6,292,610 B1 | 9/2001 | O'Rourke et al. |
| 6,306,096 B1 | 10/2001 | Seward et al. |
| 6,315,732 B1 | 11/2001 | Suorsa et al. |
| 6,379,325 B1 | 4/2002 | Benett et al. |
| 6,421,164 B2 | 7/2002 | Tearney et al. |
| 6,494,836 B2 | 12/2002 | Ogawa |
| 6,575,965 B1 | 6/2003 | Benett et al. |
| 6,585,660 B2 | 7/2003 | Dorando et al. |
| 6,618,916 B1 | 9/2003 | Eberle et al. |
| 6,659,957 B1 | 12/2003 | Vardi et al. |
| 6,779,257 B2 | 8/2004 | Kiepen et al. |
| 6,783,494 B2 | 8/2004 | Ogawa |
| 6,907,163 B2 | 6/2005 | Lewis |
| 6,948,859 B2 | 9/2005 | Anderson |
| 7,082,238 B2 | 7/2006 | Nishimura |
| 7,184,148 B2 | 2/2007 | Alphonse |
| 7,190,464 B2 | 3/2007 | Alphonse |
| 7,242,480 B2 | 7/2007 | Alphonse |
| 7,242,832 B2 | 7/2007 | Carlin et al. |
| 7,245,789 B2 | 7/2007 | Bates et al. |
| 7,417,740 B2 | 8/2008 | Alphonse et al. |
| 7,447,388 B2 | 11/2008 | Bates et al. |
| 7,527,594 B2 | 5/2009 | Vardi et al. |
| 7,599,588 B2 | 10/2009 | Eberle et al. |
| 7,660,492 B2 | 2/2010 | Bates et al. |
| 7,881,573 B2 | 2/2011 | Eberle et al. |
| 2001/0021843 A1 | 9/2001 | Bosselmann et al. |
| 2002/0039463 A1 | 4/2002 | Degertekin et al. |
| 2002/0041735 A1 | 4/2002 | Cai et al. |
| 2003/0026546 A1 | 2/2003 | Deliwala |
| 2003/0187369 A1 | 10/2003 | Lewis et al. |
| 2004/0067000 A1 | 4/2004 | Bates et al. |
| 2004/0116800 A1 | 6/2004 | Helfer et al. |
| 2004/0182315 A1 | 9/2004 | Laflamme, Jr. et al. |
| 2005/0131289 A1* | 6/2005 | Aharoni et al. ............... 600/407 |
| 2005/0238292 A1 | 10/2005 | Barnes et al. |
| 2006/0067616 A1 | 3/2006 | Kanji et al. |
| 2007/0116408 A1 | 5/2007 | Eberle et al. |
| 2007/0133925 A1 | 6/2007 | Bates et al. |
| 2008/0077225 A1 | 3/2008 | Carlin et al. |
| 2008/0119739 A1 | 5/2008 | Vardi et al. |
| 2009/0059727 A1 | 3/2009 | Bates et al. |
| 2010/0014810 A1 | 1/2010 | Eberle et al. |
| 2010/0087732 A1 | 4/2010 | Eberle et al. |

FOREIGN PATENT DOCUMENTS

| | | |
|---|---|---|
| DE | 2363984 A1 | 6/1975 |
| EP | 0478410 A1 | 4/1992 |
| EP | 1152240 A2 | 11/2001 |
| GB | 2270159 A | 3/1994 |
| JP | 63-54151 A | 3/1988 |
| JP | 02-503279 A | 10/1990 |
| JP | 05-015536 A | 1/1993 |
| JP | 05-220152 | 8/1993 |
| JP | 08-112289 A2 | 5/1996 |
| JP | 09-010215 A | 1/1997 |
| JP | 09-187513 A | 7/1997 |
| JP | 10-505920 | 6/1998 |
| JP | 10-507036 | 7/1998 |
| JP | 10-510364 A | 10/1998 |
| JP | 11-194280 A | 7/1999 |
| JP | 11-514432 | 12/1999 |
| WO | WO-89/07419 A1 | 8/1989 |
| WO | WO-99/58059 A1 | 11/1999 |
| WO | WO-00/49938 A1 | 8/2000 |
| WO | WO-01/21244 A1 | 3/2001 |
| WO | WO-02/19898 A3 | 3/2002 |
| WO | WO-02/054948 A1 | 7/2002 |
| WO | WO-02/075404 A1 | 9/2002 |
| WO | WO-03/057061 A1 | 7/2003 |
| WO | WO-2004/008070 | 1/2004 |
| WO | WO-2004/029667 A2 | 4/2004 |
| WO | WO-2004/032746 A2 | 4/2004 |
| WO | WO-2004/077100 A2 | 9/2004 |
| WO | WO-2004/090484 A2 | 10/2004 |
| WO | WO-2007/062050 A2 | 5/2007 |

OTHER PUBLICATIONS

"U.S. Appl. No. 09/623,248, Notice of Allowance mailed Jan. 13, 2003", 8 pgs.

"U.S. Appl. No. 09/623,248, Notice of Allowance mailed Jun. 2, 2003", 10 pgs.

"U.S. Appl. No. 09/623,248, Notice of Allowance mailed Jul. 11, 2003", 8 pgs.

"U.S. Appl. No. 09/623,248, Notice of Allowance mailed Jun. 2, 2003", 10 pgs.
"U.S. Appl. No. 09/623,248, Notice of Allowance mailed Jul. 11, 2003", 8 pgs.
"U.S. Appl. No. 09/623,248, Request for Continued Examination filed Apr. 14, 2003", 6 pgs.
"U.S. Appl. No. 09/623,248, Supplemental Notice of Allowability mailed Oct. 7, 2003", 6 pgs.
"U.S. Appl. No. 10/266,082, Amendment and Response filed Jan. 3, 2006 to Office Action mailed Oct. 4, 2005", 10 pgs.
"U.S. Appl. No. 10/266,082, Amendment and Response filed Jul. 5, 2006 to Office Action mailed Apr. 5, 2006", 9 pgs.
"U.S. Appl. No. 10/266,082, Final Office Action mailed Oct. 4, 2005", 7 pgs.
"U.S. Appl. No. 10/266,082, Notice of Allowance Aug. 26, 2004", 8 pgs.
"U.S. Appl. No. 10/266,082, Notice of Allowance mailed Jan. 12, 2005", 5 pgs.
"U.S. Appl. No. 10/266,082, Notice of Allowance mailed Jan. 16, 2007", 5 pgs.
"U.S. Appl. No. 10/266,082, Notice of Allowance mailed Mar. 22, 2007", 5 pgs.
"U.S. Appl. No. 10/266,082, Notice of Allowance mailed Sep. 22, 2006", 4 pgs.
"U.S. Appl. No. 10/266,082, Office Action mailed Apr. 5, 2006".
"U.S. Appl. No. 10/685,226, Advisory Action mailed Apr. 17, 2006", 4 pgs.
"U.S. Appl. No. 10/685,226, Final Office Action mailed Jan. 13, 2006", 7 pgs.
"U.S. Appl. No. 10/685,226, Non Final Office Action mailed Jan. 18, 2007", 6 pgs.
"U.S. Appl. No. 10/685,226, Non Final Office Action mailed Jun. 15, 2005", 12 pgs.
"U.S. Appl. No. 10/685,226, Non Final Office Action mailed Jul. 24, 2006", 9 pgs.
"U.S. Appl. No. 10/685,226, Notice of Allowance mailed Oct. 18, 2007", 5 pgs.
"U.S. Appl. No. 10/685,226, Response filed Mar. 13, 2006 to Final Office Action mailed", 12 pgs.
"U.S. Appl. No. 10/685,226, Response filed Oct. 14, 2005 to Non Final Office Action mailed Jun. 15, 2005", 15 pgs.
"U.S. Appl. No. 10/685,226, Response filed Apr. 18, 2007 to Non-Final Office Action mailed Jan. 18, 2007", 10 pgs.
"U.S. Appl. No. 11/285,449 Notice of Allowance mailed on May 27, 2009", 8 pgs.
"U.S. Appl. No. 11/285,499, Amendment and Response filed May 27, 2008 to Final Office Action mailed Jan. 25, 2008", 9 pages.
"U.S. Appl. No. 11/285,499, Final Office Action mailed Jan. 25, 2008", 11 pgs.
"U.S. Appl. No. 11/285,499, Non Final Office Action mailed May 16, 2007", 24 pgs.
"U.S. Appl. No. 11/285,499, Non-Final Office Action mailed May 16, 2007", 24 pgs.
"U.S. Appl. No. 11/285,499, Non-Final Office Action mailed on Nov. 13, 2008", 10 pgs.
"U.S. Appl. No. 11/285,499, Response filed Oct. 16, 2007 to Non-Final Office Action mailed May 16, 2007", 11 pgs.
"U.S. Appl. No. 11/285,499, Response filed Apr. 13, 2009 to Non Final Office Action mailed Nov. 13, 2008", 14 pgs.
"U.S. Appl. No. 11/674,568, Restriction Requirement mailed Sep. 17, 2007", 6 pgs.
"U.S. Appl. No. 11/674,568, Restriction Requirement mailed Sep. 17, 2007", 6 pgs.
"U.S. Appl. No. 11/674,568, Notice of Allowance Mailed Jun. 25, 2008", 5 pgs.
"U.S. Appl. No. 11/674,568, Non-Final Office Action Mailed Jan. 7, 2008", 15 pgs.
"U.S. Appl. No. 12/020,736, Non Final Office Action mailed Dec. 10, 2010", 11 pgs.
"U.S. Appl. No. 12/263,978, Notice of Allowance mailed Sep. 22, 2009", 15 Pgs.
"U.S. Appl. No. 12/572,511 Notice of Allowance mailed Sep. 23, 2010", 6 Pgs.

"U.S. Appl. No. 12/572,511, Non-Final Office Action mailed Jun. 1, 2010", 9 pgs.
"U.S. Appl. No. 12/572,511, Response filed 09-01-10 to Non Final Office Action mailed 06-01-10", 9 pgs.
"U.S. Appl. No. 12/572,511, Response filed May 17, 2010 to Restriction Requirement mailed May 10, 2010", 7 pgs.
"U.S. Appl. No. 12/572,511, Restriction Requirement mailed May 10, 2010", 5 pgs.
"U.S. Appl. No. 11/674,568, Response filed Apr. 21, 2008", 7 pgs.
"Canadian Patent Application No. 2,348,580, Office Action mailed Feb. 20, 2007", 2 pgs.
"Canadian Patent Application No. 2,348,580, Response filed Aug. 16, 2007 to Office Action mailed Feb. 20, 2007", 7 pgs.
"European Application Serial No. 03756904.3 Office Action mailed Nov. 3, 2009", 2 pgs.
"European Application Serial No. 06838195.3, Office Action mailed Jul. 27, 2009", 4 pgs.
"European Application Serial No. 99950325.3, Communication dated Jul. 28, 2004", 5 pgs.
"European Application Serial No. 99950325.3, Response filed Feb. 7, 2005 to Official Action mailed Jul. 28, 2004", 11 pgs.
"European Application Serial No. EP05024287, European Search Report mailed Dec. 16, 2005", 3 pgs.
"International Application Serial No. PCT/US2006/045080, Partial International Search Report mailed Mar. 9, 2007"3 pgs.
"International Preliminary Examination Report (IPER)", PCT/US03/31280, (Feb. 1, 2005), 16.
"International Search Report and Written Opinion for Application No. PCT/US2006/045080", 16 Pages.
"Japanese Application Serial No. 2000-547913, Office Action mailed on Jun. 23, 2009", 3 pgs.
"Japanese Application Serial No. 2000-547913, Office Action Mailed Feb. 13, 2009", 3 pgs.
"Japanese Application Serial No. 2004-543092, Office Action Mailed Nov. 17, 2009", 12 pgs.
"PCT U.S. Appl. No. PCT/US2003/031280, Amendment and Response filed Jan. 19, 2005 to Written Opinion mailed Jan. 14, 2005", 15 pgs.
"PCT U.S. Appl. No. PCT/US2003/031280, International Search Report mailed Jul. 19, 2004", 8 pgs.
"PCT U.S. Appl. No. PCT/US2003/031280, Written Opinion mailed Jan. 14, 2005", 16 pgs.
"PCT U.S. Appl. No. PCT/US2006/045080, International Search Report mailed May 16, 2007", 6 pgs.
"PCT U.S. Appl. No. PCT/US2006/045080, mailed May 16, 2007", 16 pgs.
"PCT Notification of Transmittal of the International Search Report or the Declaration", European Patent Office, PCT/US03/31280, (Jul. 19, 2004), 9 pages.
"PCT Written Opinion", PCT/US03/31280, (Jan. 14, 2005), 7 pages.
"Published International Search Report for PCT/US2003/031280 (WO 2004/032746 A3)", (Apr. 22, 2007), 7 pgs.
"Tissue Characterization through Ultrasonic Backscatter", [online]. [retrireved Sep. 25, 2002]. Retrieved from the Internet: <URL: http://www.brl.uiuc.edu/Projects/backscatter.htm>, (2002), pp. 1-5.
Bates, K. N., "A High Acuity 3D Acoustic Imaging System", *Proceedings., 1995 IEEE Ultrasonics Symposium, 2,* (Nov. 7-10, 1995), 1245-1250.
Bates, K. N., "A One Dimensional Phased Array Imaging System", *Ph.D. Dissertation*Applied Physics, Standford University, (1982).
Bates, K. N., et al., "Peoats and Esoats", IEEE Ultrasonics Symposium Proceedings, 1979, (Sep. 26-28, 1979), 189-194.
Bates, K. N., "Tolerance Analysis for Phased Arrays", *Acoustic Imaging,* 9, (1980), 239-262.
Bates, Kenneth N., et al., "Digitally Controlled Electronically Scanned and Focused Ultrasonic Imaging System", *IEEE Ultrasonics Symposium Proceedings, 1979,* (Sep. 26-28, 1979), 216-220.
Blotekjaer, K., "Theoretical concepts of a novel Vernier-based fringe-counting fibre optic sensor", *IEE Proceedings, Optoelectronics, 144(3),* (Jun. 1997), 126-129.

Brady, G. P., et al., "Simultaneous measurement of strain and temperature using the first-and second-order diffraction wavelengths of Bragg gratings", *IEE Proceedings, Optoelectronics, 144(3)*, (Jun. 1997), 156-161.

Buma, T., et al., "A high frequency ultrasound array element using thermoelastic expansion in PDMS", *Proceedings of the 2001 IEEE Ultrasonics Symposium, 2*, (Oct. 7-10, 2001), 1143-1146.

Buma, T., et al., "A high frequency ultrasound array element using thermoelastic expansion in PDMS", *2001 IEEE Ultrasonics Symposium. Proceedings. An International Symposium, 2(2)*, (Oct. 7-10, 2001), 1143-1146.

Buma, T., et al., "A high-frequency, 2-D array element using thermoelastic expansion in Pdms" *IEEE Transactions on Ultrasonics, Ferroelectrics and Frequency Control, 50(9)*, (Sep. 2003), 1161-1176.

Buma, T., et al., "High Frequency Ultrasonic Imaging Using Optoacoustic Arrays", *Proceedings of the Proceeding of the 2002 IEEE Ultrasonics Symposium, 1*, Invited paper, (Oct. 8-11, 2002), 571-580.

Buma, T., et al., "High Frequency Ultrasound Array Element using Thermoelastic *Expansion in an Elastomeric Film", Applied Physics Letters, 79(4)*, (Jul. 23, 2001), 548-550.

Buma, T., et al., "High-frequency ultrasound imaging using optoacoustic arrays", *Proceedings of the SPIE—The International Society for Optical Engineering, 4687*, (2002), 99-109.

Buma, T., et al., "Thermoelastic Expansion versus Piezoelectricity for High Frequency 2-D Arrays", *IEEE Transactions on Ultrasonics, Ferroelectrics and Frequency Control, 50(8)*, (Aug. 2003), 1065-1068.

Buma, T., et al., "Thermoelastic Generation of Continuous Lamb Waves for Microfluidic Devices", *Proceeding of the 2003 IEEE Ultrasonics Symposium*, (2003), 150-153.

Buma, T., et al., "Thermoelastic Generation of Ultrasound Using anErbium Doped Fiber Amplifier", *Proceeding of the 1999 IEEE Ultrasonics Symposium, 2*, (Oct. 17-20, 1999), 1253-1256.

Davis, M. A, et al., "Simultaneous measurement of temperature and strain using fibre Bragg gratings and Brillouin scattering", *IEE Proceedings, Optoelectronics, 144(3)*, (Jun. 1997), 151-155.

Feced, R., et al., "Advances in high resolution distributed temperature sensing using the time-correlated single photon counting technique", *IEE Proceedings, Optoelectronics, 144(3)*, (Jun. 1997), 183-188.

Furstenau, N., et al., "Extrinsic Fabry-Perot interferometer vibration and acoustic sensor systems for airport ground traffic monitoring", *IEE Proceedings, Optoelectronics, 144(3)*, (Jun. 1997), 134-144.

Hamilton, J. D., et al., "An active optical detector for high frequency ultrasound imaging", *Proceedings of the 1997 IEEE Ultrasonics Symposium, 1*, (Oct. 5-8, 1997), 753-756.

Hamilton, J. D., et al., "High frequency optoacoustic arrays using etalon detection", *IEEE Transactions on Ultrasonics, Ferroelectrics and Frequency Control, 47(1)*, (Jan. 2000), 160-169.

Hamilton, J. D., et al., "High Frequency Ultrasound Imaging Using an Active optical Detector", *IEEE Transactions on Ultrasonics, Ferroelectrics and Frequency Control UFFC-45*, (1998), 719-727.

Hamilton, J. D., et al., "High Frequency Ultrasound Imaging with Optical Arrays", *IEEE Transactions on Ultrasonics, Ferroelectrics and Frequency Control, 45(1)*, (Jan. 1998), 216-235.

Hamilton, J. D., et al., "Optical Arrays for High Frequency Ultrasound Imaging", Proceedings of the 1996 *IEEE Ultrasonics Symposium*, (1996), 1419-1422.

Karl, W Clem, "Multi-Sensor Fusion for Atherosclerotic Plaque Characterization", Boston Univ—MDSP, 15 pages, (obtained from the Internet on Sep. 25, 2002, http://www.censsis.neu/Education/StudentResearch/2001/posters/weisensell)r!.pdf.

Komiyama, N., et al., "Tissue Characterization of Atherosclerotic Plaques by Intravascular Ultrasound Radiofrequency Signal Analysis: An In Vitro Study of Human Coronary Arteries", *Entrez-PubMed*—(http://www.ncbi.nlm.nih.gov/entrez/query)—viewed web site on Sep. 25, 2002, pp. 1-2.

Krass, S., et al., "P3.4 Pattern Reconition Algorithms for Tissue Characterisation in Intracoronary Ultrasound Imaging: Test Data Set and Results of Computerised Texture Analysis", *2nd Medical Clinic*, Univ-Mainz, Germany—(http://www.uni-mainz.de/Cardio/incis/Data/p3_4.htm)—view web site on Sep. 25, 2002, pp. 1-3.

Lockey, R. A, et al., "Multicomponent time-division-multiplexed optical fibre laser Doppler anemometry", *IEE Proceedings, Optoelectronics, 144(3)*, (Jun. 1997), 168-175.

Macpherson, W. N, et al., "Phase demodulation in optical fibre Fabry-Perot sensors with inexact phase steps", *IEE Proceedings, Optoelectronics, 144(3)*, (Jun. 1997), 130-133.

Mcculloch, S., et al., "Development of a fibre optic micro-optrode for intracellular pH measurements", *IEE Proceedings, Optoelectronics, 144(3)*, (Jun. 1997), 162-167.

Mintz, Gary S., et al., "American College of Cardiology Clenical Expert Consensus Document on Standards for Acquisition, Measurement and Reporting of Intravascular Ultrasound Studies (IVUS)", *Journal of the American College of Cardiology, 37(5)*, (Apr. 2001), 1478-1492.

O'Donnell, M., "New Imaging Technologies for Ultrasonography", J Med Ultrason., *27(4), Presented at the 73rd Japan Society of Ultrasound in Medicine Meeting*, Invited Paper, (2000), 356-357.

O'Donnell, M., et al., "Optoacoustics: high frequency ultrasonic array imaging", *Proceedings of 17th International Congress on Acoustics, vol. IV, Biomedicine, Acoustics in Medicine*, Invited Presentation at the 17th Intl Congress on Acoustics, Rome, (Sep. 2-7, 2001), 2-3.

Othonos, a., et al., "In Section 7.9 Bragg Gating Fiber Laser Sensors from Fiber Bragg Gratings: fundamentals and applications in telecommunications and sensing", (*1999 Artech House, Inc.*), 355-367.

Pepine, Carl J., et al., "Improving Diagnostic and Therapeutic Outcomes Through Advanced Intravascular Imaging", *Vascular Technologies, Inc.*, (1989).

Scully, P. J., "UV Laser Photo-induced Refractive Index Changes in Poly-Methyl-MethAcrylate and Plastic Optical Fibres for Application as Sensors and Devices", *Central Laser Facility Annual Report*, 1999/2000, (1999-2000), 145-147.

Spisar, M., et al., "Stabilized, Resonant Optoacoustic Array Detectors for Medical Imaging", *Proceedings of the World Congress on Ultrasonics*, Paris, France, (Sep 7-10, 2003), 25-28.

Stefanadis, C., et al., "Identification and Stabilization of Vulnerable Atherosclerotic Plaques: The Role of Coronary Thermagraphy and External Heat Delivery", *Identification and Stabilization of Vulnerable Atherosclerotic Plaques IHJ*—(viewed web site on Sep. 25, 2002), http://www.indianheartjournal.org, (2001), 1-10.

Surowiec, J., et al., "A Novel Miniature Optical Fibre Probe for MHz Frequency Ultrasound", *Proceedings, IEEE Ultrasonics Symposium*, vol. 2, (Nov. 3-6, 1996, San Antonio, TX), (1996), 1051-1054.

Takahashi, N., et al., "Underwater Acoustic Sensor using Fiber Bragg Grating", *Optical Review*, 4(6), (Jan. 6,1998), 691-694.

Tanaka, S., et al., "Fibre optic spectral polarimetry for sensing multiple stress-loaded locations along a length of fibre", IEE Proceedings, Optoelectronics, 144(3), (Jun. 1997), 176-182.

Wahle, a., et al., "Accurate Visualization and Quantification of Coronary Vasculature by 3-D/4-D Fusion from Biplane Angiography and Intravascular Ultrasound", *In: Biomonitoring and Endoscopy Technologies*; I. Gannot et al., eds, (Jul. 5-6, 2000), 144-155.

Yoshino, T., et al., "Spiral fibre microbend sensors", *IEE Proceedings, Optoelectronics, 144(3)*, (Jun. 1997), 145-150.

\* cited by examiner

SYSTEMS AND METHODS FOR MINIMALLY-INVASIVE OPTICAL-ACOUSTIC IMAGING

RELATED APPLICATION

This application is a continuation of U.S. patent application Ser. No. 12/263,978, filed Nov. 3, 2008, issuing on Feb. 9, 2010 as U.S. Pat. No. 7,660,492, which is a continuation of U.S. patent application Ser. No. 11/674,568, which was filed on Feb. 13, 2007, issuing on Nov. 4, 2008 as U.S. Pat. No. 7,447,388, which is incorporated herein by reference, and which is, in turn a continuation of U.S. patent application Ser. No. 10/266,082, which was filed on Oct. 7, 2002, issuing on Jul. 17, 2007 as U.S. Pat. No. 7,245,789, which is also incorporated herein by reference.

FIELD OF THE INVENTION

This document relates generally to imaging, and particularly, but not by way of limitation, to systems and methods for minimally-invasive optical-acoustic imaging.

BACKGROUND

Vardi et al. PCT Patent Application No. PCT/US99/04913, which published on 18 Nov. 1999 as International Publication No. WO 99/58059, discusses an optical-acoustic imaging device. In that document, which is incorporated herein by reference in its entirety, including its disclosure of a guidewire optical-acoustic imaging device, an elongated imaging guidewire includes an elongated optical fiber driven by light from a laser. A distal end of the guidewire includes a polyvinyldiene fluoride (PVDF) film piezoelectric ultrasound transducer. The ultrasound transducer transmits ultrasound to an imaging region of interest about the distal tip of the guidewire, and also receives the returned ultrasound energy. The received ultrasound energy deforms a Fiber Bragg Grating (FBG or "Bragg grating") at the distal end of the guide wire, which, in turn, modulates the optical signal through the optical fiber. Imaging information about the region of interest is then obtained at the proximal end of the guidewire from the modulated optical signal.

Among other things, the present applicant has recognized that a piezoelectric ultrasound transducer may be difficult to integrate with a minimally-invasive guidewire because of electrical signal losses in ultrafine electrical conductors extending longitudinally through the guidewire assembly. Moreover, the present applicant has recognized that the field of view of the Vardi et al. device may be limited by the size of aperatures around the PVDF ultrasound transducers and/or the spacing between FBGs. Furthermore, the present applicant has recognized that the sensitivity of the Vardi et al. device may limit its usefulness in an imaging application. For these and other reasons, the present applicant has recognized that there is an unmet need in the art for improved systems and methods for performing optical-acoustic imaging.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconciliable inconsistencies, the usage in this document controls. In this document, the term "minimally-invasive" refers to techniques that are less invasive than conventional surgery; the term "minimally-invasive" is not intended to be restricted to the least-invasive technique possible.

1. Examples of Fiber Bragg Grating Acousto-Optic Sensors

Figure 1:
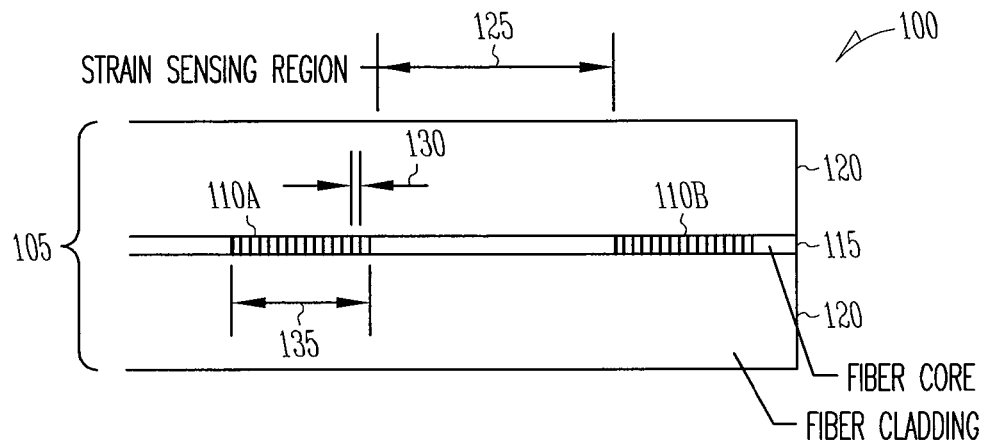
FIG. 1 is a cross-sectional side view illustrating generally, by way of example, but not by way of limitation, one example of an FBG strain sensor in an optical fiber.

FIG. 1 is a cross-sectional side view illustrating generally, by way of example, but not by way of limitation, one example of a strain-detecting FBG sensor 100 in an optical fiber 105. FBG sensor 100 senses acoustic energy received from a nearby area to be imaged, and transduces the received acoustic energy into an optical signal within optical fiber 105. In the example of FIG. 1, FBG sensor 100 includes Bragg gratings 110A-B in an optical fiber core 115 surrounded by an optical fiber cladding 120. Bragg gratings 110A-B are separated by a strain sensing region 125, which, in one example, is about a millimeter in length. This example senses strain by detecting an "optical displacement" between these gratings 110A-B.

A fiber Bragg grating can be conceptualized as a periodic change in the optical index (which is inversely proportional to the speed of light in the material) of a portion of the optical fiber core 115. Light of a specific wavelength traveling down such a portion of core 115 will be reflected; the period (distance) 130 of the change in the optical index determines the particular wavelength of light that will be reflected. The degree of index change and the length 135 of the grating determine the ratio of light reflected to that transmitted through the grating.

Figure 2:
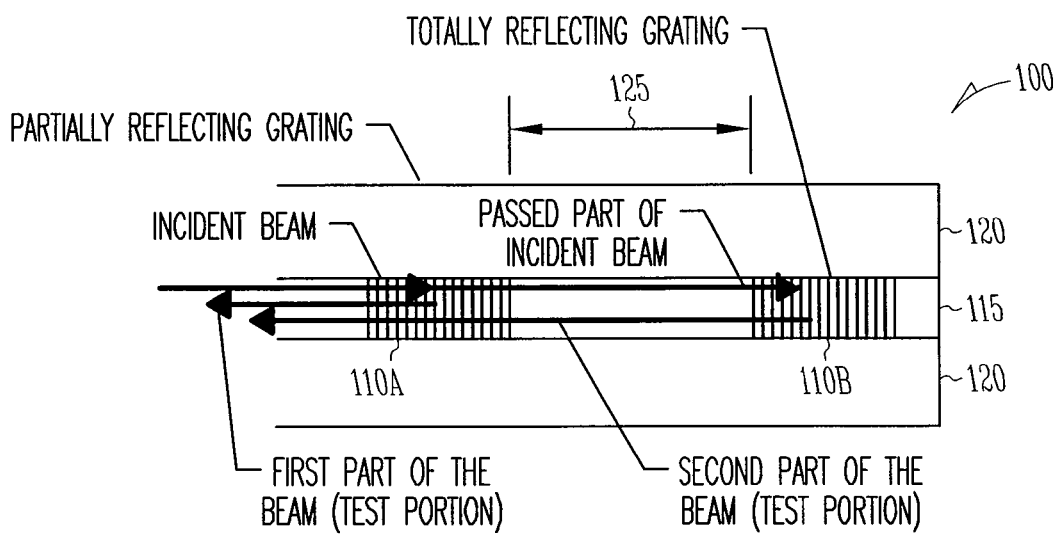
FIG. 2 is a cross-sectional side view illustrating generally, by way of example, but not by way of limitation, an example of an FBG grating interferometer sensor.

FIG. 2 is a cross-sectional side view illustrating generally, by way of example, but not by way of limitation, an operative example of an interferometric FBG sensor 100. The example of FIG. 2 includes two FBGs 110A-B. FBG 110A is partially reflective at a specific wavelength of light passing through fiber core 115. FBG 110B is substantially fully reflective of such light. This interferometric arrangement of FBGs 110A-B is capable of discerning the "optical distance" between FBGs 110A-B with extreme sensitivity. The "optical distance" is a function of the velocity of light in the material of fiber core 115 as well as the length 125 between FBGs 110A-B. Thus, a change in the velocity of light can induce a change in optical distance even though the physical distance 125 between FBGs 110A-B has not changed.

An interferometer such as FBG sensor 100 can be conceptualized as a device that measures the interference between two paths taken by an optical beam. A partially reflecting FBG 110A (or a partially reflecting mirror) is used to split the incident beam of light into two parts. In an interferometer, one part of the beam travels along a path that is kept constant (i.e., a control path) and the other part travels a path where some change is to be monitored (i.e., a test path). Using partially reflecting FBG 110A (or a partially reflecting mirror, either of which may alternatively be in addition to FBG 110A), the two parts of the beam are combined. If the two paths are identical, the parts combine to form the original beam. If the two paths are different, the two parts will add or subtract from each other. This addition or subtraction is known as interference. A complete subtraction is called a null and occurs at a precise wavelength of light for a given difference in paths. Measuring the wavelength where this null occurs yields an indication of the difference in optical paths between the two beams. In such a manner, an interferometer such as FBG sensor 100 senses small changes in distance, such as a change in the optical distance 125 between FBGs 110A-B resulting from received ultrasound or other received acoustic energy.

In one example, such as illustrated in FIG. 2, the interferometric FBG sensor 100 causes the interference between that portion of the optical beam that is reflected off the first (partially reflective) FBG 110A with that reflected from the second (substantially fully reflective) FBG 110B. The wavelength of light where an interferometric null will occur is very sensitive to the "optical distance" 125 between the two FBGs 110A-B. This interferometric FBG sensor 100 of FIG. 2 has another very practical advantage. In this example, the two optical paths along the fiber core 115 are the same, except for the sensing region between FBGs 110A-B. This shared path ensures that any optical changes in the shared portion of optical fiber 105 will have substantially no effect upon the interferometric signal; only the change in the sensing region between FBGs 125 is sensed.

2. Examples of Devices and Methods Improving FBG Reception

In one example, an FBG sensor 100 senses strain generated by ultrasound or other acoustic energy received from a nearby imaging region to be visualized and, in response, modulates an optical signal in an optical fiber. Increasing the sensitivity of the FBG sensor 100 provides improved imaging. A first example of increasing sensitivity is to increase the amount of strain induced in the FBG sensor 100 for a given dynamic pressure provided by the acoustic energy. A second example is to increase the modulation of the optical signal for a given change in strain of the FBG sensor 100.

One technique of increasing the strain induced in the FBG sensor 100 is to design the physical attributes of the FBG sensor 100 to increase the degree of strain for a given externally applied acoustic field. In one such example, increased strain is obtained by using material that has a high degree of strain for a given stress. Calculations indicate that over two orders of magnitude increase in strain vs. stress (also referred to as "compliance") is obtained by using an optical grade plastic, rather than glass, in the fiber core 115 of the FBG sensor 100. One example of a suitable optical grade plastic used in fiber core 115 is poly-methyl-methacrylate (PMMA).

Figure 3A:
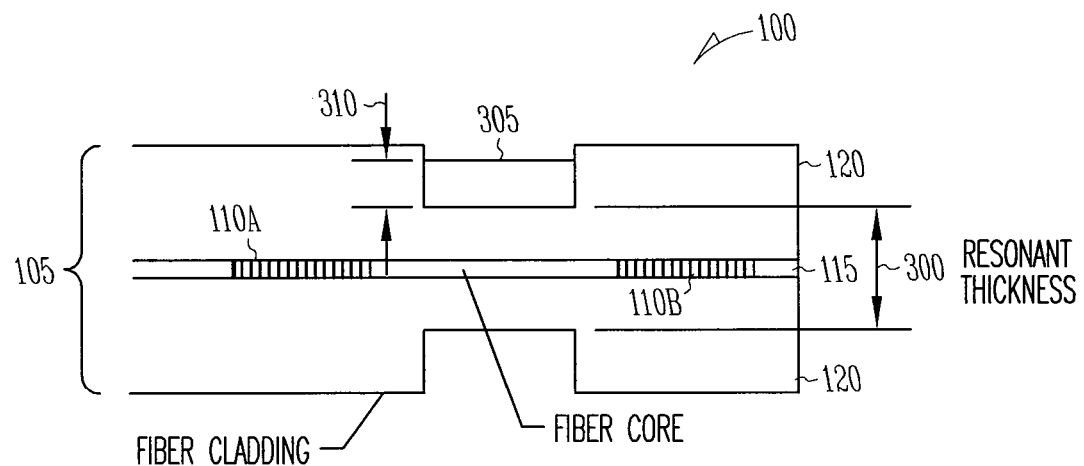
FIG. 3A is a cross-sectional schematic diagram illustrating generally one example of a distal portion of an imaging guidewire that combines an acousto-optic FBG sensor with an photoacoustic transducer.

In a second example, the FBG sensor 100 is shaped so as to increase the strain for a given applied acoustic pressure field. FIG. 3A is a cross-sectional schematic diagram illustrating one such example in which the FBG sensor 100 is shaped such that it mechanically resonates at the frequency of the acoustic energy received from the nearby imaging region, thereby resulting in increased strain. In the example of FIG.

3A, all or a portion of the strain sensing region between FBGs 110A-B is selected to provide a resonant thickness 300 that promotes mechanical resonance of the received acoustic energy, thereby increasing the resulting strain sensed by FBG sensor 100. In one example, such as illustrated in FIG. 3A, this is accomplished by grinding or otherwise removing a portion of fiber cladding 120, such that the remaining thickness of fiber core 115 and/or fiber cladding 120 between opposing planar (or other) surfaces is selected to mechanically resonate at the frequency of the acoustic energy received from the nearby imaging region.

In one example, for a particular material, mechanical resonance is obtained by making the resonant thickness 300 of the strain sensing region substantially the same thickness as ½ the acoustic wavelength (or an odd integer multiple thereof) in the material(s) of FBG sensor 100 at the acoustic center frequency of the desired acoustic frequency band received from the imaging region. In other examples, such as for other materials, the resonant thickness 300 is selected to match a different proportion of the acoustic wavelength that obtains the desired mechanical resonance for that material. Calculations indicate that obtaining such mechanical resonance will increase the strain sensitivity by about an order of magnitude over that of a sensor that is not constructed to obtain such mechanical resonance.

In a third example, a special coating 305 is applied to the FBG sensor 100 to increase the acoustic pressure as seen by the FBG sensor 100 over a band of acoustic frequencies, thereby improving its sensitivity over that band. The difference between the mechanical characteristics of water (or tissue and/or blood, which is mostly comprised of water) and glass material of the optical fiber 105 carrying the FBG sensor 100 is typically so significant that only a small amount of acoustic energy "enters" the FBG sensor 100 and thereby causes strain; the remaining energy is reflected back into the biological or other material being imaged. For a particular range of acoustic frequencies, one or more coatings 305 of specific thickness 310 and/or mechanical properties (e.g., the particular mechanical impedance) of the coating material can dramatically reduce such attenuation due to the different mechanical characteristics. One example uses quarter wave matching, providing a coating 305 of a thickness 310 that is approximately equal to one quarter of the acoustic signal wavelength received from the region being imaged. Using such matching, the sensitivity of the FBG sensor 100, over a given band of acoustic frequencies of interest, is expected to increase by about an order of magnitude.

In one example, using the above-discussed quarter wave matching and sensor shaping techniques, the sensitivity of the FBG sensor 100 approaches that of a piezoelectric transducer. Additionally using optical grade plastic for fiber core 115, in conjunction with one or the other of these techniques, will further increase the sensitivity of the FBG sensor 100.

Additionally (or alternatively) to the above techniques of increasing the strain of the FBG sensor 100 for a particular level of acoustic energy, in one example, the optical sensitivity of the FBG sensor 100 to strain is increased, thereby increasing the sensitivity of the FBG sensor 100 to an acoustic field. In one example, this is accomplished by improved techniques of optical wavelength discrimination, such as by using a fiber-based Mach-Zehnder interferometer or by construction of improved optical fiber geometries that increase the optical sensitivity of the FBG sensor 100 to strain.

3. Examples of Systems and Methods Improving Ultrasound Transmission

The present applicant has recognized that while it may be possible to implement an imaging guidewire that transmits ultrasound using a piezoelectric transducer, such a design may involve a trade-off. If the piezoelectric transducer radiates the ultrasonic energy in a broad radial pattern, imaging quality may be degraded. Conversely, using smaller piezoelectric transducers to transmit ultrasound may require significant electrical voltages in a guidewire in order to achieve needed acoustic transmit energy. This is because a smaller transducer has a higher electrical impedance, needing a higher voltage to achieve the same acoustic power. Such a guidewire must also use materials of sufficient dielectric properties to ensure patient safety. Moreover, adding electrically conducting wires to a guidewire assembly complicates its manufacture.

However, optical energy can be converted to acoustic energy. In one example, therefore, such problems are overcome using an optical-to-acoustic transmitter, which, in one example, is integrated with an acoustic-to-optical receiver such as FBG sensor 100.

Figure 3B:
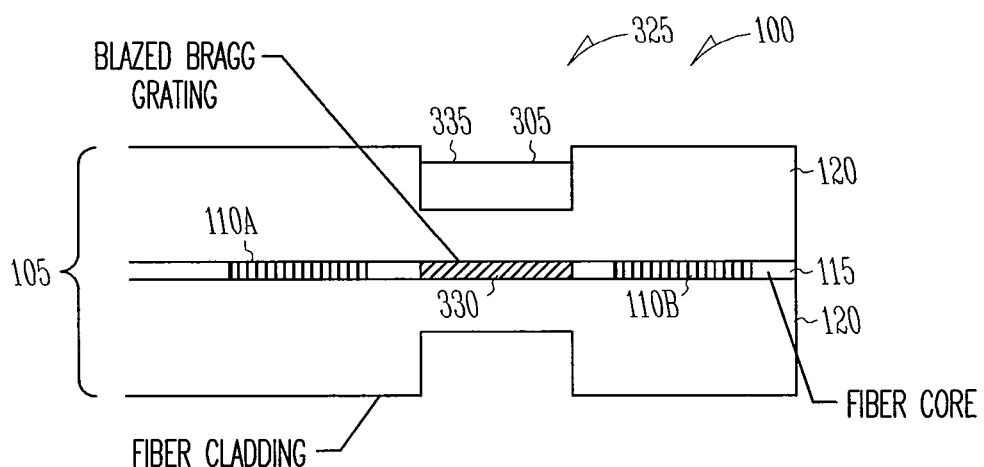
FIG. 3B is a cross-sectional schematic diagram illustrating generally one example of a distal portion of an imaging guidewire that combines an acousto-optic FBG sensor with an photoacoustic transducer.

FIG. 3B is a cross-sectional schematic diagram illustrating generally one example of a distal portion of an imaging guidewire that combines an acousto-optic FBG sensor 100 with an photoacoustic transducer 325. In this example, photoacoustic transducer 325 includes a blazed Bragg grating 330. In the illustrative example of FIG. 3B, blazed Bragg grating 330 is implemented in the strain sensitive region of the FBG sensor 100, between FBGs 110A-B, however, this is not a requirement. Unlike an unblazed Bragg grating, which typically includes impressed index changes that are substantially perpendicular to the longitudinal axis of the fiber core 115 of the optical fiber 105, the blazed Bragg grating 330 includes obliquely impressed index changes that are at a nonperpendicular angle to the longitudinal axis of the optical fiber 105.

A standard unblazed FBG partially or substantially fully reflects optical energy of a specific wavelength traveling down the axis of the fiber core 115 of optical fiber 105 back up the same axis. Blazed FBG 330 reflects this optical energy away from the longitudinal axis of the optical fiber 105. For a particular combination of blaze angle and optical wavelength, the optical energy will leave blazed FBG 330 substantially normal (i.e., perpendicular) to the longitudinal axis of the optical fiber 105. In the illustrative example of FIG. 3B, an optically absorptive photoacoustic material 335 (also referred to as a "photoacoustic" material) is placed on the surface of optical fiber 105. The optically absorptive photoacoustic material 335 is positioned, with respect to the blazed grating 330, so as to receive the optical energy leaving the blazed grating. The received optical energy is converted in the optically absorptive material 335 to heat that expands the optically absorptive photoacoustic material 335. The optically absorptive photoacoustic material 335 is selected to expand and contract quickly enough to create and transmit an ultrasound or other acoustic wave that is used for acoustic imaging of the region of interest about the distal tip (or other desired portion) of the imaging guidewire. In one example, the optically absorptive photoacoustic material 335 is the same material as the acoustic matching material 305 discussed above.

Figure 4:
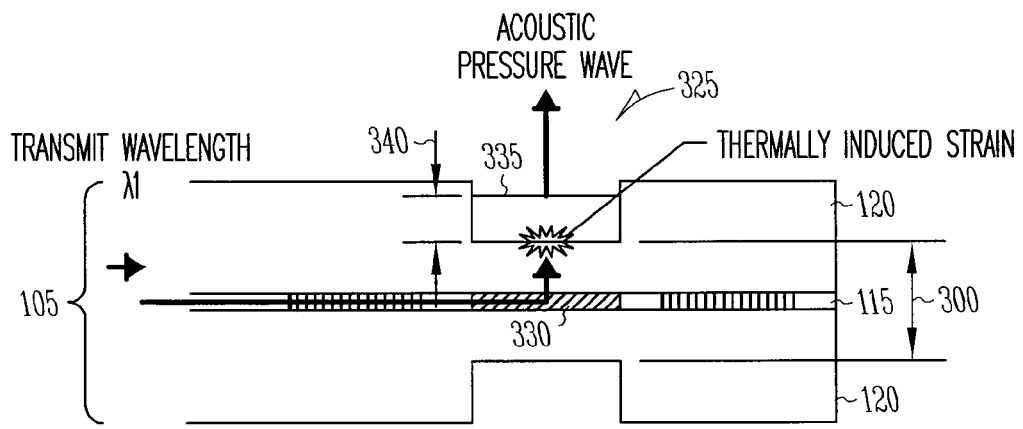
FIG. 4 is a cross-sectional schematic diagram illustrating generally one example of the operation of a blazed grating FBG photoacoustic transducer.

FIG. 4 is a cross-sectional schematic diagram illustrating generally one example of the operation of photoacoustic transducer 325 using a blazed Bragg grating 330. Optical energy of a specific wavelength, $\lambda_1$, travels down the fiber core 115 of optical fiber 105 and is reflected out of the optical fiber 105 by blazed grating 330. The outwardly reflected optical energy impinges on the photoacoustic material 335. The photoacoustic material 335 then generates a responsive acoustic impulse that radiates away from the photoacoustic material 335 toward nearby biological or other material to be imaged. Acoustic energy of a specific frequency is generated by optically irradiating the photoacoustic material 335 at a pulse rate equal to the desired acoustic frequency.

In another example, the photoacoustic material 335 has a thickness 340 (in the direction in which optical energy is received from blazed Bragg grating 330) that is selected to increase the efficiency of emission of acoustic energy. In one example, thickness 340 is selected to be about ¼ the acoustic wavelength of the material at the desired acoustic transmission/reception frequency. This improves the generation of acoustic energy by the photoacoustic material.

In yet a further example, the photoacoustic material is of a thickness 300 that is about ¼ the acoustic wavelength of the material at the desired acoustic transmission/reception frequency, and the corresponding glass-based optical fiber sensing region resonant thickness 300 is about ½ the acoustic wavelength of that material at the desired acoustic transmission/reception frequency. This further improves the generation of acoustic energy by the photoacoustic material and reception of the acoustic energy by the optical fiber sensing region.

In one example of operation, light reflected from the blazed grating excites the photoacoustic material in such a way that the optical energy is efficiently converted to substantially the same acoustic frequency for which the FBG sensor is designed. The blazed FBG and photoacoustic material, in conjunction with the aforementioned FBG sensor, provide both a transmit transducer and a receive sensor, which are harmonized to create an efficient unified optical-to-acoustic-to-optical transmit/receive device. In one example, the optical wavelength for sensing is different from that used for transmission. In a further example, the optical transmit/receive frequencies are sufficiently different that the reception is not adversely affected by the transmission, and vice-versa.

Figure 5:
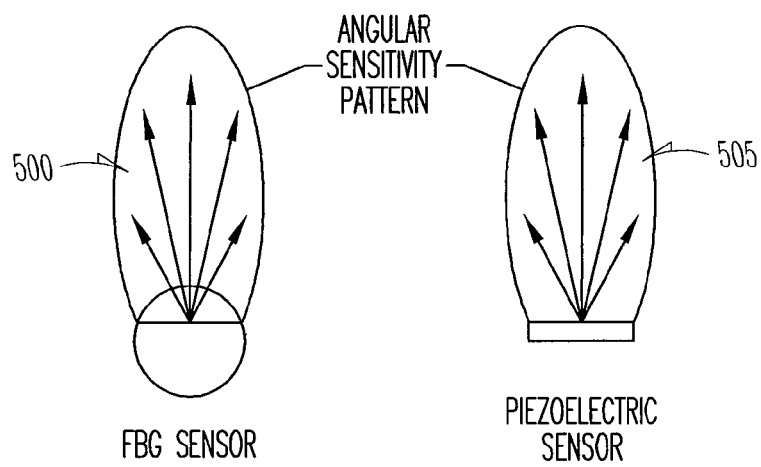
FIG. 5 is a schematic diagram comparing an expected angular sensitivity pattern of an exemplary blazed FBG optical-to-acoustic and acoustic-to-optical combined device to that of a piezoelectric sensor.

FIG. 5 is a schematic diagram comparing an expected angular sensitivity pattern of an exemplary blazed FBG optical-to-acoustic and acoustic-to-optical combined device 500 to that of a piezoelectric transducer 505. As seen in the example of FIG. 5, the optical-to-acoustic-to-optical sensor assembly 500 is expected to be capable of operating over a specific angular range that is substantially similar to that of the piezoelectric transducer 505 of similar dimensions. Therefore, in one example, the blazed FBG optical-to-acoustic and acoustic-to-optical combined device 500 is capable of using conventional intravascular ultrasound ("IVUS") techniques.

Figure 6:
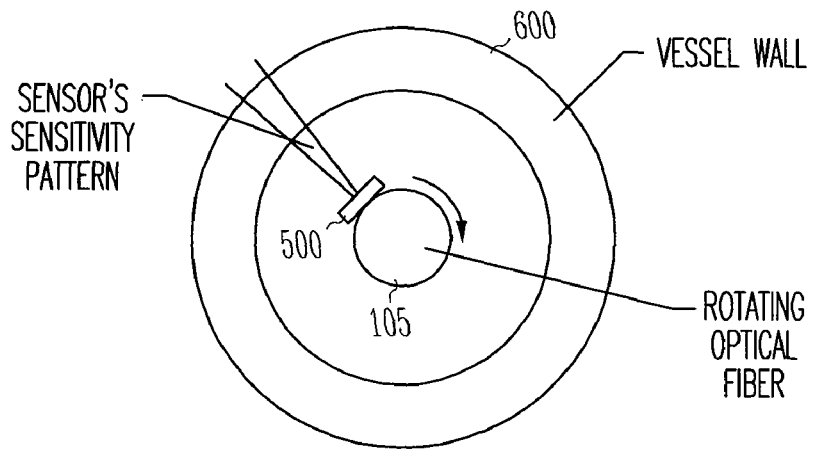
FIG. 6 is a schematic diagram illustrating generally one technique of generating an image by rotating the blazed FBG optical-to-acoustic and acoustic-to-optical combined transducer and displaying the resultant series of radial image lines to create a radial image.
Figure 7:
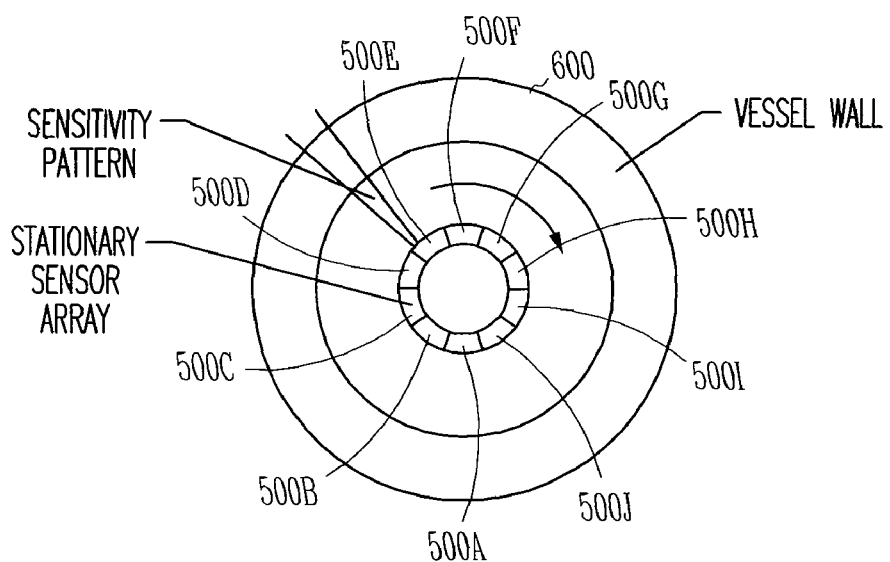
FIG. 7 is a schematic diagram that illustrates generally one such phased array example, in which the signal to/from each array transducer is combined with the signals from the other transducers to synthesize a radial image line.

FIG. 6 is a schematic diagram illustrating generally one technique of generating an image of a vessel wall 600 by rotating the blazed FBG optical-to-acoustic and acoustic-to-optical combined transducer 500 and displaying the resultant series of radial image lines to create a radial image. In another example, phased array mages are created using a substantially stationary (i.e., non-rotating) set of multiple FBG sensors, such as FBG sensors 500A-J. FIG. 7 is a schematic diagram that illustrates generally one such phased array example, in which the signal to/from each array transducer 500A-J is combined with the signals from one or more other transducers 500A-J to synthesize a radial image line. In this example, other image lines are similarly synthesized from the array signals, such as by using specific changes in the signal processing used to Combine These Signals.

4. Examples of Guidewire Design

Figure 8:
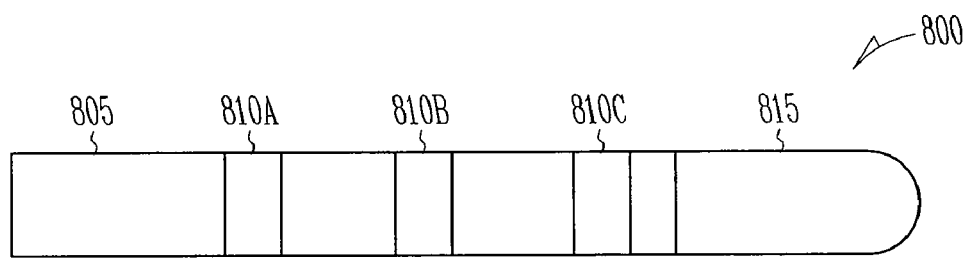
FIG. 8 is a schematic diagram that illustrates generally an example of a side view of a distal portion of a guidewire.

FIG. 8 is a schematic diagram that illustrates generally an example of a side view of a distal portion 800 of an imaging guidewire 805 or other elongate catheter (in one example, the guidewire 805 is capable of being used for introducing and/or guiding a catheter or other medical instrument, e.g., over the guidewire 805). In this example, the distal portion 800 of the imaging guidewire 805 includes one or more imaging windows 810A, 810B, . . . , 810N located slightly or considerably proximal to a distal tip 815 of the guidewire 805. Each imaging window 810 includes one or more optical-to-acoustic transducers 325 and a corresponding one or more separate or integrated acoustic-to-optical FBG sensors 100. In one example, each imaging window 810 includes an array of blazed FBG optical-to-acoustic and acoustic-to-optical combined transducers 500 (such as illustrated in FIG. 7) located slightly proximal to distal tip 815 of guidewire 805 having mechanical properties that allow the guidewire 805 to be guided through a vascular or other lumen. In one example, the different imaging windows 810A, 810B, . . . , 810N are designed for different optical wavelengths, such that individual windows can be easily addressed by changing the optical wavelength being communicated through fiber core 115.

Figure 9:
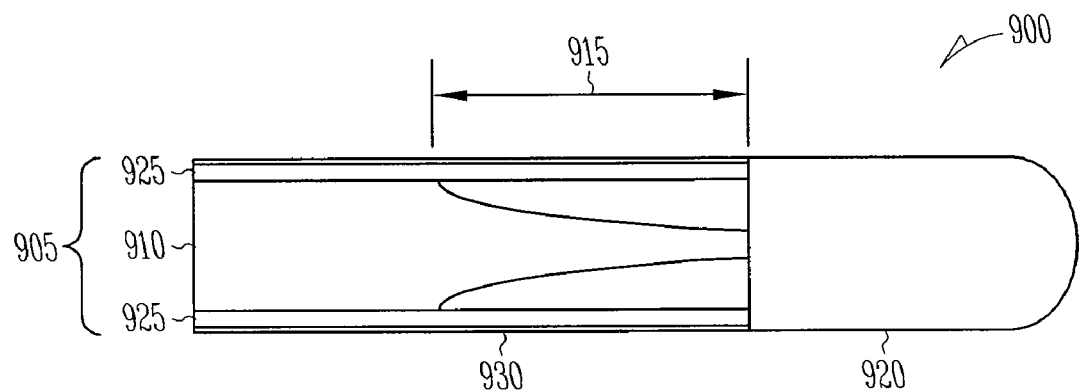
FIG. 9 is a schematic diagram that illustrates generally one example of a cross-sectional side view of a distal portion of a guidewire.

FIG. 9 is a schematic diagram that illustrates generally one example of a cross-sectional side view of a distal portion 900 of another guidewire 905. In this example, the guide-wire 905 includes a solid metal or other core 910 that tapers down in diameter (e.g., from an outer diameter of about 0.011 inches) at a suitable distance 915 (e.g., about 50 cm) from the distal tip 920, to which the tapered core 910 is attached. In this example, optical fibers 925 are distributed around the outer circumference of the guidewire core 910, and attached to the distal tip 920. In this example, the optical fibers 925 are at least partially embedded in a polymer matrix or other binder material that bonds the optical fibers 925 to the guidewire core 910 and/or the distal tip 920. The binder material may also contribute to the torsion response of the resulting guidewire assembly 905. In one example, the optical fibers 925 and binder material is overcoated with a polymer or other coating 930, such as for providing abrasion resistance, optical fiber protection, and/or friction control. In this example, the composite structure of the distal region 900 of the guidewire 905 provides, among other things, flexibility and rotational stiffness, thereby allowing the guidewire 905 to be maneuvered to an imaging region of interest within a vascular or any other lumen.

Figure 10:
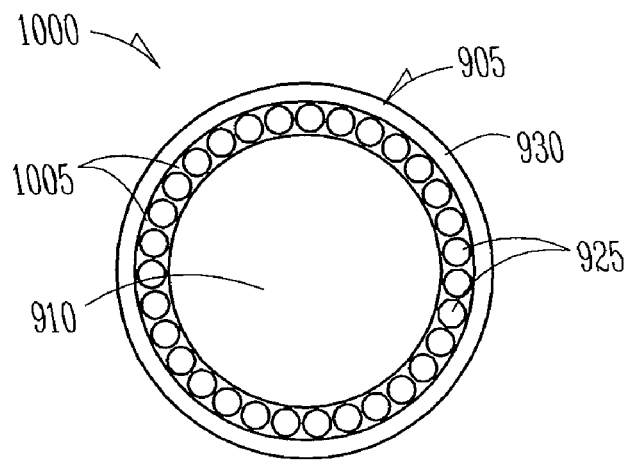
FIG. 10 is a schematic diagram that illustrates generally one example of a cross-sectional end view of a proximal portion of a guidewire.

FIG. 10 is a schematic diagram that illustrates generally one example of a cross-sectional end view of a proximal portion 1000 of guidewire 905, which includes guidewire core 910, optical fibers 925, binder material 1005, and outer coating 930. In this example, but not by way of limitation, the diameter of the core 910 is about 11/1000 inch, the diameter of the optical fibers 925 is about (1.25)/1000 inch, and the optional outer coating 930 is about (0.25)/1000 inch thick.

Figure 11:
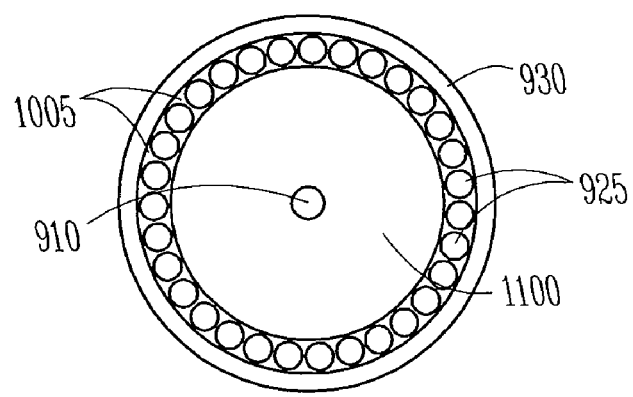
FIG. 11 is a schematic diagram that illustrates generally one example of a cross-sectional end view of a distal portion of a guidewire.

FIG. 11 is a schematic diagram that illustrates generally one example of a cross-sectional end view of distal portion 900 of guidewire 905, e.g., adjacent to distal tip 920. In this example, but not by way of limitation, the diameter of core 910 has tapered down to about (1.5)/1000 inch, circumferentially surrounded by a void 1100 of about the same diameter (e.g., about 11/1000 inch) as the core 910 near the proximal end 100 of the guidewire 905. In this example, the optical fibers 925 are circumferentially disposed in the binder material 1005 around the void 1100. Binder material 1005 provides structural support. Optical fibers 925 are optionally overlaid with the outer coating 930.

Figure 12:
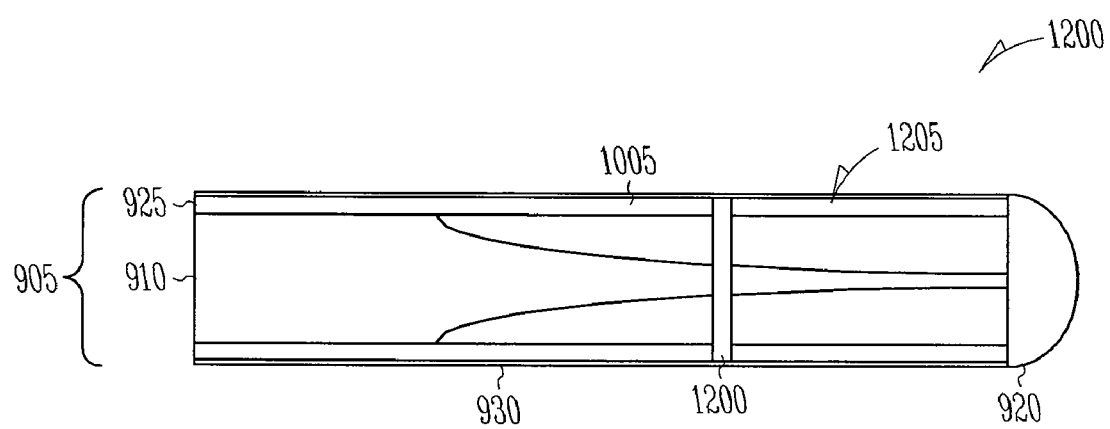
FIG. 12 is a schematic diagram that illustrates generally one example of a cross-sectional side view of a distal portion of a guidewire.

FIG. 12 is a schematic diagram that illustrates generally one example of a cross-sectional side view of a distal portion 900 of a guidewire 905. In this example, at least one metallic or other bulkhead 1200 is provided along the tapered portion of the guidewire core 910. The optical fibers 925 and binder 1005 are attached to a proximal side of the bulkhead 1200 near its circumferential perimeter. A distal side of the bulkhead 1200 is attached, near its circumferential perimeter, to a coil winding 1205 that extends further, in the distal direction, to a ball or other distal tip 920 of the guidewire 905.

5. Examples of Acoustic Transducer Construction

In one example, before the acoustic transducer(s) is fabricated, the guidewire 905 is assembled, such as by binding the optical fibers 925 to the core 910 and distal tip 920 or bulkhead 1200, and optionally coating the guidewire 905. The optoacoustic transducer(s) are then integrated into the guidewire assembly 905, such as by grinding one or more grooves in the guidewire at the locations of the optoacoustic transducer windows 810. In a further example, the depth of these groove(s) in the optical fiber(s) 925 defines the resonant structure(s) of the optoacoustic transducer(s).

After the optoacoustic transducer windows 810 have been defined, the FBGs added to one or more portions of the optical fiber 925 within such windows 810. In one example, the FBGs are created using an optical process in which the portion of the optical fiber 925 is exposed to a carefully controlled pattern of UV radiation that defines the Bragg gratings. Then, a photoacoustic material is deposited or otherwise added in the transducer windows 810 over respective Bragg gratings. One example of a suitable photoacoustic material is pigmented polydimethylsiloxane (PDMS), such as a mixture of PDMS, carbon black, and toluene. Thus, in this example, the FBGs are advantageously constructed after the major elements of the guidewire are mechanically assembled into the guidewire assembly 905.

6. Examples of Proximal End Interface

Figure 13A:
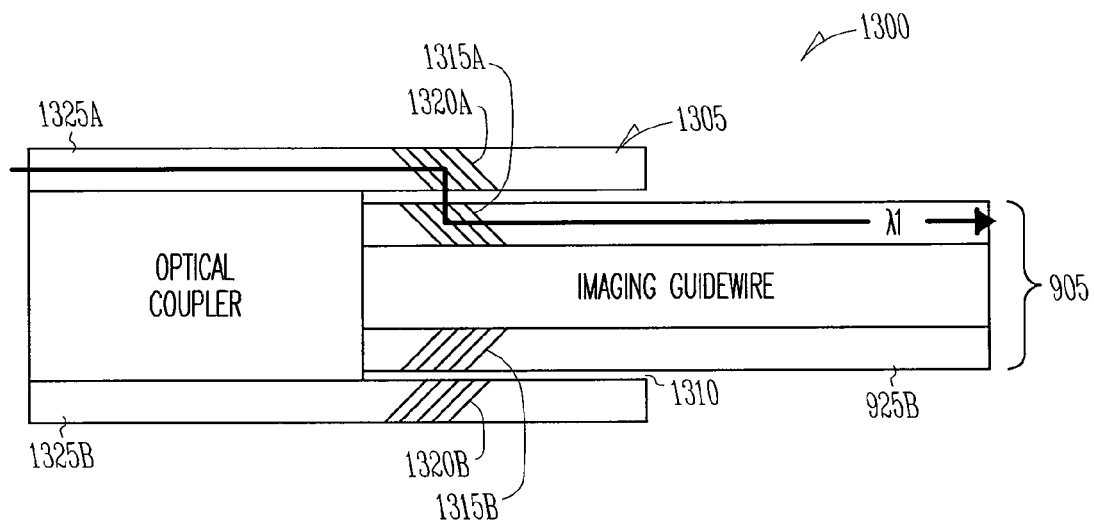
FIG. 13A is a cross-sectional schematic diagram illustrating generally one example of a proximal portion of a guidewire, which is communicatively coupled to an instrumentation/control interface via an optical coupler.
Figure 13B:
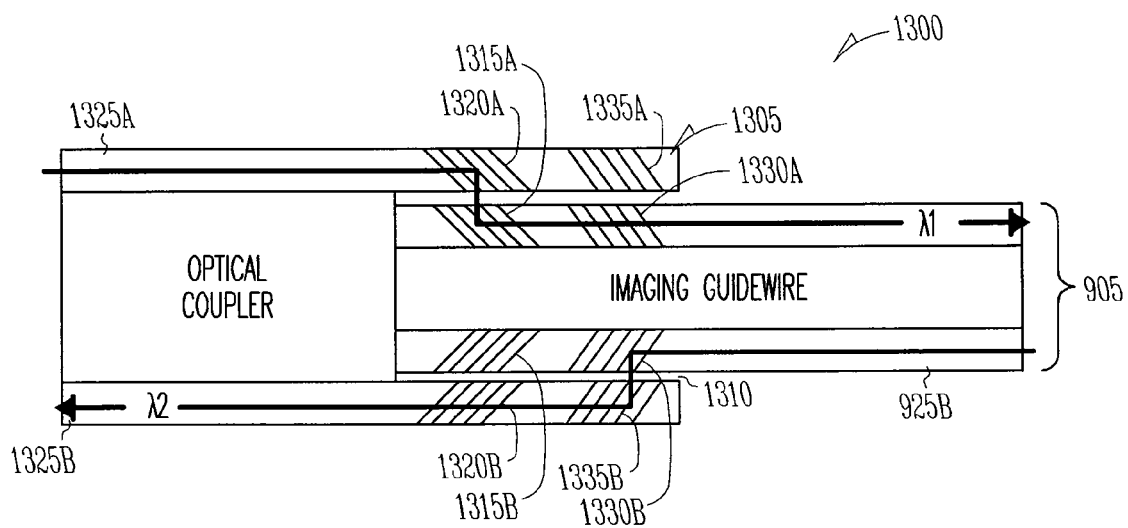
FIG. 13B is a cross-sectional schematic diagram illustrating generally a further example of a proximal portion of a guidewire that is communicatively coupled to an instrumentation/control interface using an optical coupler.

In one example, the guidewire 905 allows for over-the-guidewire or other insertion of a catheter at the proximal end of the guidewire. Therefore, in such an example, the guidewire 905 (including any proximal end interface) has an outer diameter that is less than or equal to the inner diameter (e.g., 0.014 inches) of a catheter to allow the catheter with a similarly-sized inner diameter to travel over the guidewire 905. FIGS. 13A and 13B provide illustrative examples of an optical coupler that easily engages and disengages guidewire 905. Among other things, this facilitates over-the-guidewire catheter insertion, and viewing an imaging region either before, during, or after such a catheter is inserted over-the-guidewire.

FIG. 13A is a cross-sectional schematic diagram illustrating generally one example of a proximal portion 1300 of guidewire 905, which is communicatively coupled to an instrumentation/control interface via an optical coupler 1305. In this example, proximal portion 1300 of guidewire 905 is received within a receptacle 1310 portion of optical coupler 1305, and includes one or more blazed FBGs 1315 to couple light into and/or out of one or more respective optical fibers 925 of guidewire 905. Optical coupler 1305 includes one or more corresponding blazed FBGs 1320 to couple light into and/or out of one or more respective optical fibers 1325 of optical coupler 1305. In the example of FIG. 13A, the FBGs 1320 of optical coupler 1305 are located substantially adjacent to corresponding FBGs 1315 of guidewire 905 when guidewire 905 is engaged within receptacle 1310 of optical coupler 1305. Although FIG. 13A illustrates a multiple-fiber embodiment of guidewire 905, the illustrated techniques for coupling to an instrumentation/control interface are also applicable to a guidewire that includes a single optical fiber.

FIG. 13B is a cross-sectional schematic diagram illustrating generally a further example of a proximal portion 1300 of guidewire 905 that is communicatively coupled to an instrumentation/control interface using an optical coupler 1305. In the example of FIG. 13B, at least one optical fiber 925 transmits light at a different wavelength from that at which it receives light. Therefore, such an optical fiber 925 includes two separate blazed FBGs that couple light into and out of each such optical fiber 925. For example, as illustrated in FIG. 13B, optical fiber 925A includes a first blazed FBG 1315A operating at the transmit wavelength, and a second blazed FBG 1330A operating at the receive wavelength. Optical coupler 1305 includes a corresponding first blazed FBG 1320A operating at the transmit wavelength and a second blazed FBG 1335A operating at the receive wavelength. When a proximal portion 1300 of guidewire 905 is fully inserted into receptacle 1310, blazed FBGs 1320A and 1315A are located substantially adjacent to each other, and blazed FBGs 1335A and 1330A are located substantially adjacent to each other. Similarly, optical fiber 925B and optical coupler 1305 respectively include substantially adjacent transmit FBGs 1315B and 1320B and substantially adjacent receive FBGs 1330B and 1335B.

For additional optoacoustic transducer windows 810 at or near the distal portion 900 or elsewhere along guidewire 905, corresponding additional blazed FBGs may similarly be included on optical coupler 1305 at the appropriate wavelength for transmitting and/or receiving optical energy with respect to such additional optoacoustic transducer windows 810. Moreover, optical coupler 1305 need not be located exactly at the proximal end of the guidewire 905, but may instead be located anywhere near the proximal portion 1300 of the guidewire 905 or even further toward the distal portion 900 of the guidewire 905. Also, alignment of the optical coupler 1305 to guidewire 905 need not be limited to butting guidewire 905 into receptacle 1310 of optical coupler 1305; any other alignment mechanism and/or technique is also included.

7. Examples of Process and Control Imaging Electronics

Figure 14A:
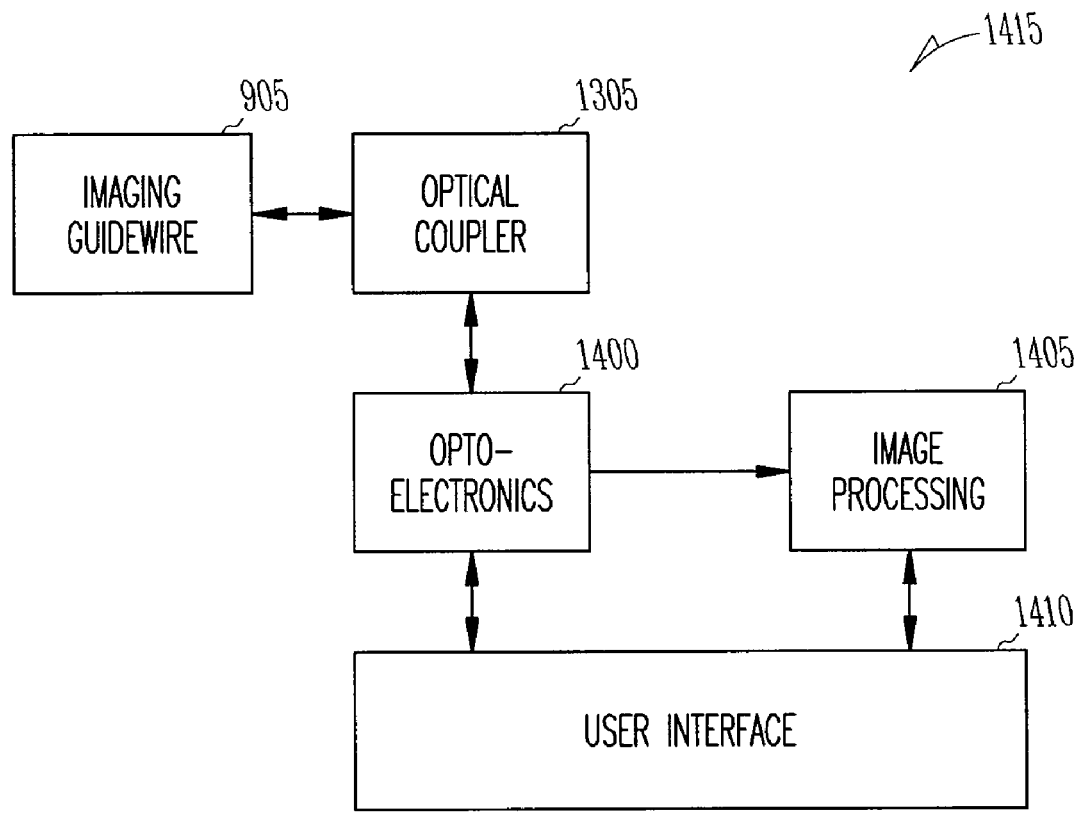
FIG. 14A is a block diagram illustrating generally one example of the imaging guidewire and associated interface components.

FIG. 14A is a block diagram illustrating generally one example of the imaging guidewire 905 and associated interface components. The block diagram of FIG. 14A includes the imaging guidewire 905, which is coupled by optical coupler 1305 to an optoelectronics module 1400. The optoelectronics module 1400 is coupled to an image processing module 1405 and a user interface 1410 that includes a display providing a viewable still and/or video image of the imaging region near one or more acoustic-to-optical transducers using the acoustically-modulated optical signal received therefrom. In one example, the system 1415 illustrated in the block diagram of FIG. 14A uses an image processing module 1405 and a user interface 1410 that are substantially similar to existing acoustic imaging systems.

Figure 14B:
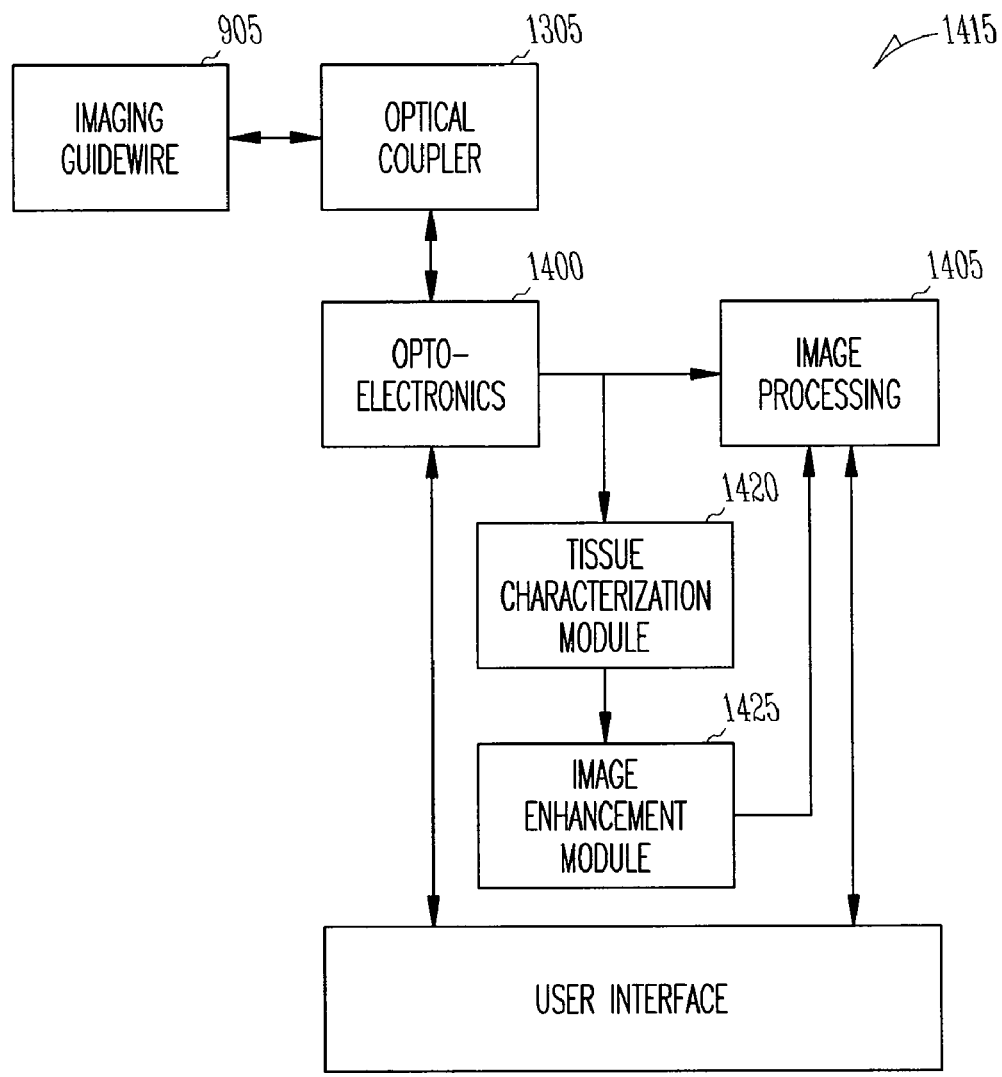
FIG. 14B is a block diagram illustrating generally another example of the imaging guidewire and associated interface components, including tissue characterization and image enhancement modules.

FIG. 14B is a block diagram illustrating generally another example of the imaging guidewire 905 and associated interface components. In this example, the associated interface components include a tissue (and plaque) characterization module 1420 and an image enhancement module 1425. In this example, an input of tissue characterization module 1420 is coupled to an output from optoelectronics module 1400. An output of tissue characterization module 1420 is coupled to at least one of user interface 1410 or an input of image enhancement module 1425. An output of image enhancement module 1425 is coupled to user interface 1410, such as through image processing module 1405.

In this example, tissue characterization module 1420 processes a signal output from optoelectronics module 1400. In one example, such signal processing assists in distinguishing plaque from nearby vascular tissue. Such plaque can be conceptualized as including, among other things, cholesterol, thrombus, and loose connective tissue that build up within a blood vessel wall. Calcified plaque typically reflects ultrasound better than the nearby vascular tissue, which results in high amplitude echoes. Soft plaques, on the other hand, produce weaker and more texturally homogeneous echoes. These and other differences distinguishing between plaque deposits and nearby vascular tissue are detected using tissue characterization signal processing techniques.

For example, such tissue characterization signal processing may include performing a spectral analysis that examines the energy of the returned ultrasound signal at various frequencies. A plaque deposit will typically have a different spectral signature than nearby vascular tissue without such plaque, allowing discrimination therebetween. Such signal processing may additionally or alternatively include statistical processing (e.g., averaging, filtering, or the like) of the returned ultrasound signal in the time domain. Other signal processing techniques known in the art of tissue characterization may also be applied. In one example, the spatial distribution of the processed returned ultrasound signal is provided to image enhancement module 1425, which provides resulting image enhancement information to image processing module 1405. In this manner, image enhancement module 1425 provides information to user interface 1410 that results in a displaying plaque deposits in a visually different manner (e.g., by assigning plaque deposits a discernable color on the image) than other portions of the image. Other image enhancement techniques known in the art of imaging may also be applied. In a further example, similar techniques are used for discriminating between vulnerable plaque and other plaque, and enhancing the displayed image provide a visual indicator assisting the user in discriminating between vulnerable and other plaque.

8. Examples of Opto-Electronics Module

The opto-electronics module 1400 may include one or more lasers and fiber optic elements. In one example, such as where different transmit and receive wavelengths are used, a first laser is used for providing light to the guidewire 905 for the transmitted ultrasound, and a separate second laser is used for providing light to the guidewire 905 for being modulated by the received ultrasound. In this example, a fiber optic multiplexer couples each channel (associated with a particular one of the guidewire's optical fibers 925) to the transmit and receive lasers and associated optics. This reduces system complexity and costs.

In one example, the sharing of transmit and receive components by multiple guidewire channels is possible at least in part because the acoustic image is acquired over a relatively short distance (e.g., millimeters). The speed of ultrasound in a human or animal body is slow enough to allow for a large number of transmit/receive cycles to be performed during the time period of one image frame. For example, at an image depth (range) of about 2 cm, it will take ultrasonic energy approximately 26 microseconds to travel from the sensor to the range limit, and back. In one such example, therefore, an about 30 microseconds transmit/receive (T/R) cycle is used. In the approximately 30 milliseconds allotted to a single image frame, up to 1,000 T/R cycles can be carried out. In one example, such a large number of T/R cycles per frame allows the system to operate as a phased array even though each sensor is accessed in sequence. Such sequential access of the photoacoustic sensors in the guidewire permits (but does not require) the use of one set of T/R opto-electronics in conjunction with a sequentially operated optical multiplexer.

9. Example of Use for 3-Dimensional (3-D) Imaging

In one example, instead of presenting one 2-D slice of the anatomy, the system is operated to provide a 3-D visual image that permits the viewing of a desired volume of the patient's anatomy or other imaging region of interest. This allows the physician to quickly see the detailed spatial arrangement of structures, such as lesions, with respect to other anatomy. In one example, in which the guidewire 905 includes 30 sequentially-accessed optical fibers having up to 10 photoacoustic transducer windows per optical fiber, 30×10=300 T/R cycles are used to collect the image information from all the transducer windows for one image frame. This is well within the allotted 1,000 such cycles for a range of 2 cm, as discussed above. Thus, such an embodiment allows substantially simultaneous images to be obtained from all 10 transducer windows at of each optical fiber at video rates (e.g., at about 30 frames per second for each transducer window). This allows real-time volumetric data acquisition, which offers a distinct advantage over other imaging techniques. Among other things, such real-time volumetric data acquisition allows real-time 3-D vascular imaging, including visualization of the topology of a blood vessel wall, the extent and precise location of plaque deposits, and, therefore, the ability to identify vulnerable plaque.

10. Alternate Example of Acoustic-to-Optical Receiver

Figure 15:
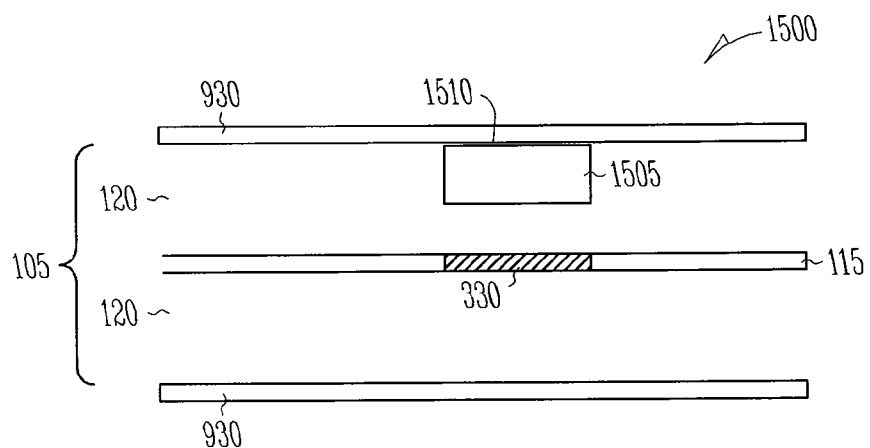
FIG. 15 is a cross-sectional schematic diagram illustrating generally one example of an alternate acoustic-to-optical transducer.

FIG. 15 is a cross-sectional schematic diagram illustrating generally one example of an alternate acoustic-to-optical transducer 1500, which in this example is integrated into an optical fiber 105, including fiber core 105 and fiber cladding 120 and covered by coating 930. In the illustrative example of FIG. 15, transducer 1500 includes a blazed FBG 330 in core 115, a translucent deformable (or empty) region 1505 in cladding 120, and an acoustically-deformable light-reflective surface region 1510 overlaying at least a portion of translucent region 1505. In one example, acoustic-to-optical transducer 1500 is fabricated in a window 810 of an imaging guidewire 805 along with an optical-to-acoustic transducer 325, which generates acoustic energy in a nearby imaging region of interest to be received by acoustic-to-optical transducer 1500.

Figure 16:
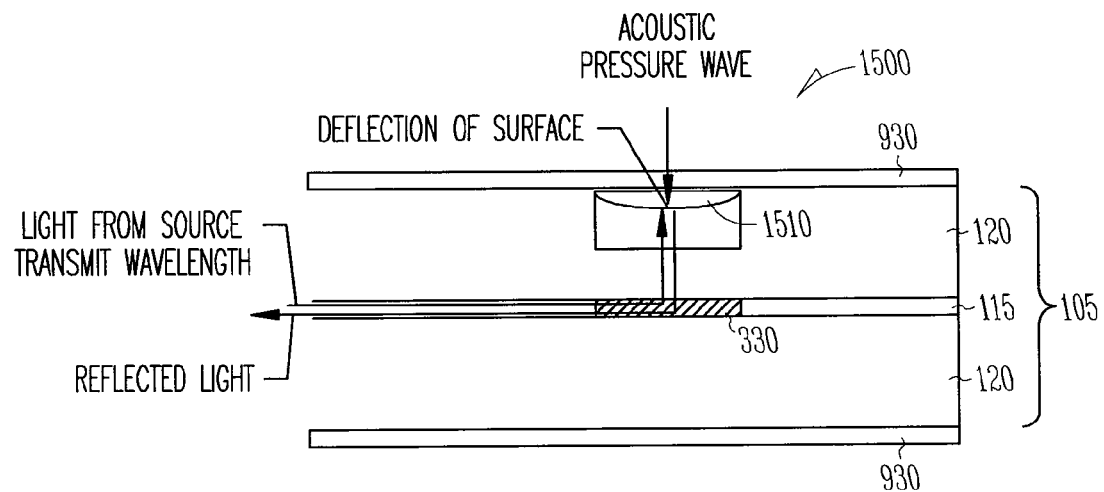
FIG. 16 is a cross-sectional schematic diagram illustrating generally one example of operation of the acoustic-to-optical transducer of FIG. 15.

FIG. 16 is a cross-sectional schematic diagram illustrating generally one example of acoustic-to-optical transducer 1500 in operation. FBG 330 receives light from a proximal end of fiber core 105, and directs the received light outward through translucent region 1505 such that the light impinges upon, and is reflected by, reflective region 1510. At least some of the reflected light is received at FBG 330 and directed back toward the proximal end of fiber core 105. As illustrated in FIG. 16, reflective region 1510 deflects in response to acoustic energy received from the nearby imaging region of interest as a result of insonification by a nearby optical-to-acoustic transducer 325. The deflection of reflective region 1510 modulates the distance that the light travels between FBG 330 and reflective region 1510. The resulting change in wavelength or intensity is monitored by interface optoelectronics coupled to a proximal end of optical fiber 105, such as using the above-described components and techniques.

As illustrated in the example of FIGS. 15 and 16, acoustic-to-optical transducer 1500 need only include a single FBG (e.g., blazed FBG 330). Moreover, acoustic-to-optical transducer 1500 need not rely on the Poisson effect in which received acoustic energy "squeezes" in a first direction, thereby modulating an interferometric strain-sensing distance in a second direction that is normal to the first direction. An acoustic-to-optical transducer using the Poisson effect typically suffers from some attenuation in translating the mechanical force from the first direction to the orthogonal second direction. As illustrated in FIG. 16, however, the acoustic-to-optical transducer 1500 detects a modulating distance that is in the substantially the same direction as the received acoustic energy. Moreover, because region 1510 is reflective, a given deflection results in a modulation of twice the number of wavelengths of light in that deflection distance. This further increases the sensitivity of acoustic-to-optical transducer 1500.

In one example, region 1505 is filled with a transparent polymer to allow optical energy to pass through. In a further example, region 1505 has a thickness 1515 that is ¼-wave resonant with the received acoustic pressure wave. In such an example, the resonance of the polymer-filled region 1505 serves to increase the motion of the reflective region 1510 over that which would occur if region 1505 were formed of glass. In a further example, the polymer-filled region 1505 includes an acoustic impedance that is close to that of water and, therefore, human or animal tissue.

11. Conclusion

Although certain of the above examples have been described with respect to intravascular imaging (e.g., for viewing and/or identifying vulnerable plaque), the present systems, devices, and methods are also applicable to imaging any other body part. For example, for example guidewire or other elongate body as discussed above could be inserted into a biopsy needle, laparoscopic device, or any other lumen or cavity for performing imaging. Moreover, such imaging need not involve insertion of an elongate body into a lumen, for example, an imaging apparatus could alternatively be wrapped around a portion of a region to be imaged.

In another example, this technology can be used to process the Doppler shift in acoustic frequency to image blood flow. The operation would be similar to that described above, however, this would increase the length of the transmitted acoustic signal, and would use known Doppler signal processing in the image processing portion of the control electronics. The transmitted acoustic signal can be lengthened by repeatedly pulsing the transmit optical energy at the same rate as the desired acoustic frequency.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects.

What is claimed is:

1. An imaging apparatus including:
an elongated body having proximal and distal ends and a plurality of longitudinally spaced apart imaging windows along at least a portion of the body, the body including at least one optical fiber, an imaging window including:
an optical-to-acoustic transducer, near the distal end of the body, configured to generate acoustic energy for imaging a region near the distal end of the body in response to a first optical signal in the optical fiber; and
an acoustic-to-optical transducer near the distal end of the body, configured to sense acoustic energy from the region near the distal end of the body and to provide a responsive second optical signal in the optical fiber.

2. The apparatus of claim 1, and a user interface, including a display configured to provide a three-dimensional image of the region near the distal end of the body using the second optical signal.

3. The apparatus of claim 1, wherein the optical-to-acoustic transducer includes a photoacoustic material that is located substantially outside of a core of the optical fiber but that is capable of receiving light from the core of the optical fiber to generate an optical-to-acoustic response.

4. The apparatus of claim 3, in which the photoacoustic material is of a thickness, in a direction substantially normal to that traveled by the acoustic energy sensed from the region near the distal end of the body, substantially equal to an odd integer multiple of ¼ the acoustic wavelength of the acoustic energy sensed from the region near the distal end of the body.

5. The apparatus of claim 3, comprising means for directing light passing along the core out of the core and into the photoacoustic material.

6. The apparatus of claim 3, comprising a blazed Bragg grating located in a core of the optical fiber, in which the blazed Bragg grating redirects light passing axially along the core out of the core and into the photoacoustic material.

7. The apparatus of claim 3, in which the elongated body provides a guidewire sized and shaped for at least one of introducing a catheter into a lumen and guiding a catheter within a lumen.

8. The apparatus of claim 7, in which the elongated body is substantially cylindrical, and in which the elongated body includes a plurality of optical fibers disposed about its cylindrical circumference.

9. The apparatus of claim 1, in which the acoustic-to-optical transducer includes at least one Bragg grating.

10. The apparatus of claim 9, in which the acoustic-to-optical transducer includes an interferometer that includes a partially reflective first Bragg grating, a substantially fully reflective second Bragg grating, and a blazed third Bragg grating disposed between the first and second Bragg gratings.

11. The apparatus of claim 9, in which the acoustic-to-optical transducer includes an acoustically deformable reflector located, with respect to the at least one Bragg grating, to reflect light received from the at least one Bragg grating.

12. The apparatus of claim 1, further including an optical coupler sized and shaped to be coupled at or near the proximal end of the elongate body to communicate of at least one of the first and second optical signals, and in which the optical coupler includes at least one blazed Bragg grating to communicate at least one of the first and second optical signals.

13. The apparatus of claim 1, in which the optical-to-acoustic transducer and the acoustic-to-optical transducer share a common photoacoustic material for generating acoustic energy and forming an acoustic matching layer.

14. The apparatus of claim 1, further including:
an optoelectronics module, configured to be optically coupled to a portion of the elongated body;
an imaging processing module, coupled to the optoelectronics module, and wherein the user interface is coupled to at least one of the optoelectronics module and the image processing module;
a tissue characterization module coupled to the optoelectronics module, the tissue characterization module configured to recognize plaque; and
an image enhancement module, coupled to the tissue characterization module and to the user interface to provide a visually distinctive display of the plaque.

15. The apparatus of claim 1, wherein the same optical fiber includes at least two imaging windows.

16. The apparatus of claim 15, wherein the at least two imaging windows included in the same optical fiber are configured to be individually addressable.

17. The apparatus of claim 16, wherein the at least two imaging windows included in the same optical fiber are configured to be individually addressed by using different wavelengths of light in the optical fiber to selectively individually address the different imaging windows.

18. The apparatus of claim 1, comprising an opto-electronics module configured to sequentially access particular imaging windows.

19. The apparatus of claim 1, wherein the opto-electronics module is configured to sequentially access particular optical fibers.

20. The apparatus of claim 1, wherein the opto-electronics module is configured to sequentially access particular imaging windows and particular optical fibers in a phased-array manner so as to provide real-time volumetric data acquisition, and comprising a display configured to render a resulting three-dimensional image.

21. The apparatus of claim 1, comprising a flexible and rotationally-stiff distal end portion providing enough flexibility and rotational stiffness to allow the distal portion to be maneuvered to an imaging region of interest within a vascular lumen.

22. An imaging guidewire, including:
an elongate substantially cylindrical guidewire core, including proximal and distal portions and a substantially cylindrical circumference; and
a plurality of elongate optical fibers, located along the cylindrical circumference of the guidewire core, the plurality of elongate optical fibers providing a plurality of longitudinally spaced apart imaging windows along at least a portion of the plurality of elongate optical fibers, an imaging window including:
an optical-to-acoustic transducer, near the distal end of the body and associated with at least one of the optical fibers, the optical-to-acoustic transducer configured to generate acoustic energy for imaging a region near the distal end of the body in response to a first optical signal.

23. The guidewire of claim 22, wherein the imaging window comprises:
an acoustic-to-optical transducer near the distal end of the body and associated with at least one of the optical fibers, the acoustic-to-optical transducer configured to sense acoustic energy from the region near the distal end of the body and to provide a responsive second optical signal.

24. The guidewire of claim 23, wherein the optical-to-acoustic transducer is configured to direct light from a core of the at least one of the fibers to a photoacoustic material located outside of the core of the at least one of the fibers.

25. The guidewire of claim 23, comprising means, located in the core of the at least one of the fibers, for directing light outside of the core and into the photoacoustic material.

26. The guidewire of claim 23, comprising a blazed Bragg grating, located in the core of the at least one of the fibers, and capable of directing light outside of the core and into the photoacoustic material.

27. The guidewire of claim 23, in which the guidewire is sized and shaped to be inserted into a blood vessel, and in which the guidewire is sized and shaped to allow over-the-guidewire insertion of a catheter when the guidewire is inserted into a blood vessel.

28. The guidewire of claim 23, in which the acoustic-to-optical transducer includes at least two blazed Bragg gratings located to cooperate interferometrically.

29. The guidewire of claim 23, in which the acoustic-to-optical transducer includes a blazed Bragg grating and an acoustically-deformable reflector located to reflect light received from the blazed Bragg grating of the acoustic-to-optical transducer.

* * * * *

UNITED STATES PATENT AND TRADEMARK OFFICE
CERTIFICATE OF CORRECTION

| | |
|---|---|
| PATENT NO. | : 8,059,923 B2 |
| APPLICATION NO. | : 12/701228 |
| DATED | : November 15, 2011 |
| INVENTOR(S) | : Kenneth N. Bates et al. |

It is certified that error appears in the above-identified patent and that said Letters Patent is hereby corrected as shown below:

On the face page, in field (74), in "Attorney, Agent, or Firm", in column 2, line 1, delete "Schwgman, Lundberg" and insert -- Schwegman, Lundberg --, therefor.

On page 3, under "Other Publications", in column 2, line 54, delete "[retrireved" and insert -- [retrieved --, therefor.

On page 3, under "Other Publications", in column 2, line 60, delete "DissertationApplied" and insert -- Dissertation, Applied --, therefor.

On page 3, under "Other Publications", in column 2, line 60, delete "Standford" and insert -- Stanford --, therefor.

On page 4, under "Other Publications", in column 1, line 34, delete "anErbium" and insert -- an Erbium --, therefor.

On page 4, under "Other Publications", in column 2, line 4, delete "Reconition" and insert -- Recognition --, therefor.

On page 4, under "Other Publications", in column 2, line 15, delete "micro-optrode" and Insert -- micro-optode --, therefor.

On page 4, under "Other Publications", in column 2, line 18, delete "Clenical" and insert -- Clinical --, therefor.

On page 4, under "Other Publications", in column 2, line 31, delete "Gating" and insert -- Grating --, therefor.

On page 4, under "Other Publications", in column 2, line 45, delete "Thermagraphy" and Insert -- Thermography --, therefor.

Signed and Sealed this
Seventh Day of February, 2012

David J. Kappos
*Director of the United States Patent and Trademark Office*

CERTIFICATE OF CORRECTION (continued)
U.S. Pat. No. 8,059,923 B2

On Sheet 10 of 11, Box "User Interface", Figure 14B, line 1, after " *[USER INTERFACE]* " insert -- 1410 --, as a reference numeral for box "User Interface".

In column 1, line 34, delete "polyvinyldiene" and insert -- polyvinylidene --, therefor.

In column 1, line 40, delete "guide wire," and insert -- guidewire, --, therefor.

In column 1, line 51, delete "aperatures" and insert -- apertures --, therefor,

In column 3, line 21, delete "irreconciliable" and insert -- irreconcilable --, therefor.

In column 4, line 35, delete "125" and insert -- 110A-B --, therefor.

In column 7, line 60, delete "Combine These Signals." and insert -- combine these signals. --, therefor.

In column 8, line 22, delete "guide-wire" and insert -- guidewire --, therefor.

In column 14, line 55, in Claim 11, delete "acoustically deformable" and insert -- acoustically-deformable --, therefor.